United States Patent
Böhringer et al.

(10) Patent No.: US 11,607,668 B2
(45) Date of Patent: Mar. 21, 2023

(54) AIR-PERMEABLE SHEET FILTER MATERIAL, METHODS FOR THE PRODUCTION AND USE THEREOF

(71) Applicant: Blücher GmbH, Erkrath (DE)

(72) Inventors: Bertram Böhringer, Wuppertal (DE);
Rainer Fischer, Neuss (DE);
Congminh Nguyen, Wuppertal (DE)

(73) Assignee: BLÜCHER GMBH

( * ) Notice: Subject to any disclaimer, the term of this patent is extended or adjusted under 35 U.S.C. 154(b) by 427 days.

(21) Appl. No.: 16/767,272

(22) PCT Filed: Sep. 3, 2018

(86) PCT No.: PCT/EP2018/073606
§ 371 (c)(1),
(2) Date: May 27, 2020

(87) PCT Pub. No.: WO2019/105611
PCT Pub. Date: Jun. 6, 2019

(65) Prior Publication Data
US 2021/0106976 A1  Apr. 15, 2021

(30) Foreign Application Priority Data

Nov. 28, 2017 (DE) .................... 10 2017 010 986.9
Jan. 17, 2018 (DE) .................... 10 2018 100 935.6

(51) Int. Cl.
*B01D 53/02* (2006.01)
*B01J 20/28* (2006.01)
(Continued)

(52) U.S. Cl.
CPC ..... *B01J 20/28052* (2013.01); *A41D 13/1192* (2013.01); *A61L 9/014* (2013.01);
(Continued)

(58) Field of Classification Search
CPC ...... B01D 2239/025; B01D 2239/0407; B01D 2239/045; B01D 2239/065;
(Continued)

(56) References Cited

U.S. PATENT DOCUMENTS

2008/0110342 A1* 5/2008 Ensor .................. D01D 5/0092
425/173
2010/0282682 A1* 11/2010 Eaton ................. B01D 39/1623
442/351
(Continued)

FOREIGN PATENT DOCUMENTS

DE 102014216979 A1 3/2016
DE 202015104218 U1 7/2016

*Primary Examiner* — Christopher P Jones
(74) *Attorney, Agent, or Firm* — Edward E. Sowers; Brannon Sowers & Cracraft PC

(57) ABSTRACT

The present invention relates to a sheet filter material, in particular having an aerosol filter function and/or a particle filter function, preferably having a protective function against chemical, biological and/or chemical harmful and toxic substances, and to a method for the production thereof. The sheet filter material is particularly suitable for producing protective equipment, protective objects, sports and leisure clothing and filters and filter materials of all types.

26 Claims, 2 Drawing Sheets

(51) Int. Cl.
    *A41D 13/11* (2006.01)
    *A61L 9/014* (2006.01)
    *B01D 39/08* (2006.01)
    *B01D 39/16* (2006.01)
    *B01D 39/20* (2006.01)
    *B01D 46/00* (2022.01)
    *B01D 46/54* (2006.01)
    *B01J 20/20* (2006.01)
    *B01J 20/26* (2006.01)
    *B32B 5/02* (2006.01)
    *B32B 5/18* (2006.01)
    *B32B 5/24* (2006.01)
    *B32B 27/40* (2006.01)

(52) U.S. Cl.
    CPC ....... *B01D 39/083* (2013.01); *B01D 39/1623* (2013.01); *B01D 39/1676* (2013.01); *B01D 39/2058* (2013.01); *B01D 46/0036* (2013.01); *B01D 46/0038* (2013.01); *B01D 46/546* (2013.01); *B01J 20/20* (2013.01); *B01J 20/267* (2013.01); *B01J 20/28011* (2013.01); *B01J 20/28035* (2013.01); *B01J 20/28045* (2013.01); *B32B 5/022* (2013.01); *B32B 5/18* (2013.01); *B32B 5/245* (2013.01); *B32B 27/40* (2013.01); *A61L 2209/14* (2013.01); *A61L 2209/22* (2013.01); *B01D 2239/025* (2013.01); *B01D 2239/045* (2013.01); *B01D 2239/0407* (2013.01); *B01D 2239/0654* (2013.01); *B01D 2239/10* (2013.01); *B01D 2239/1216* (2013.01); *B01D 2239/1233* (2013.01); *B01D 2239/1258* (2013.01); *B01D 2239/1291* (2013.01); *B01D 2275/10* (2013.01); *B32B 2266/0278* (2013.01); *B32B 2307/718* (2013.01); *B32B 2307/7145* (2013.01); *B32B 2307/724* (2013.01); *B32B 2307/732* (2013.01); *B32B 2307/758* (2013.01); *B32B 2535/00* (2013.01)

(58) Field of Classification Search
    CPC ........ B01D 2239/0654; B01D 2239/10; B01D 2239/1216; B01D 2239/1233; B01D 2239/1258; B01D 2239/1291; B01D 2275/10; B01D 39/08; B01D 39/083; B01D 39/16; B01D 39/1623; B01D 39/1676; B01D 39/2058; B01D 46/0036; B01D 46/0038; B01D 46/546; A61L 2209/14; A61L 2209/22; A61L 9/014; B01J 20/06; B01J 20/08; B01J 20/103; B01J 20/18; B01J 20/20; B01J 20/226; B01J 20/261; B01J 20/262; B01J 20/267; B01J 20/28011; B01J 20/28026; B01J 20/28035; B01J 20/28045; B01J 20/28052; B32B 2266/0278; B32B 2307/7145; B32B 2307/718; B32B 2307/724; B32B 2307/732; B32B 2307/758; B32B 2535/00; B32B 27/40; B32B 5/022; B32B 5/18; B32B 5/22; B32B 5/245

See application file for complete search history.

(56) References Cited

U.S. PATENT DOCUMENTS

| | | | |
|---|---|---|---|
| 2012/0312744 A1 | 12/2012 | Axelrod | |
| 2013/0108831 A1* | 5/2013 | Wu | D04H 1/54 428/161 |
| 2018/0111349 A1* | 4/2018 | Polidore | B32B 7/04 |
| 2020/0254371 A1* | 8/2020 | Yung | A62B 23/02 |
| 2020/0288810 A1* | 9/2020 | Baggen | A62D 5/00 |

* cited by examiner

AIR-PERMEABLE SHEET FILTER MATERIAL, METHODS FOR THE PRODUCTION AND USE THEREOF

CROSS-REFERENCES TO RELATED APPLICATIONS

This application is a National Stage filing of International Application PCT/EP 2018/073606, filed Sep. 3, 2018, entitled Air-Permeable Sheet Filter Material, Methods for the Production and Use Thereof, claiming priority to DE 10 2017 010 986.9, filed Nov. 28, 2017, and DE 10 2018 100 935.6, filed Jan. 17, 2018. The subject application claims priority to PCT/EP 2018/073606, to DE 10 2017 010 986.9 and to DE 10 2018 100 935.6, and incorporates all by reference herein, in their entirety.

BACKGROUND OF THE INVENTION

The present invention relates to the technical field of functional sheet filter materials such as in particular textile protective materials which can be used in the defense or civil sector, for example for the production of protective equipment and protective clothing as well as functional sports and leisure apparel as well as for various filter applications.

In this context, the present invention relates to a sheet filter material per se which is in particular equipped with an aerosol function or particle filter function, respectively, or with a protective function in relation to chemical, biological, or radioactive (nuclear) harmful and toxic substances, respectively, or provides a corresponding filtering or protective function, respectively, wherein the sheet filter material according to the invention has a special construction based on a foam-based or foam-shaped, respectively, support material (i.e. carrier material), on the one hand, and a nanofiber layer that is assigned to the foam-based or foam-shaped support material, on the other hand.

The present invention moreover also relates to a method for producing the sheet filter material according to the invention, as well as to special uses of the sheet filter material according to the invention, in particular for the production of protective equipment or protective items, respectively, sports or leisure wear, respectively, or sports or leisure equipment, respectively, as well as for the production of filters and filter materials of all manner. The present invention moreover also relates to protective equipment as well as protective items and filters as well as filter materials which comprise the sheet filter material according to the invention, or which are produced while using the sheet filter material according to the invention.

High requirements in terms of providing a positive wear comfort (such as, for example, a high level of breathability as well as a comfortable wear experience), on the one hand, and of providing therebeyond a protective function in relation to external effects such as environmental influences (for example wind, rain, or the like), as well as in relation to toxic substances (such as can arise, for example, with a view to defense personnel or soldiers, respectively, in defensive or offensive action, respectively, or else with a view to personnel such as firefighters or the like which are in action in an emergency or a fire), on the other hand, are generally set for functional sheet filter materials such as can be used, for example, in the textile industry sector for producing protective clothing for the defense sector, as well as moreover also for the sports sector or leisure sector, respectively, for producing functional items of clothing or items of equipment, respectively. In this context, a large challenge in the development of corresponding sheet filter materials lies in unifying the diametrically opposed properties of a high level of wear comfort as well as an effective protective function in one and the same material, this in the case of materials known in the prior art to date often not having been successful to a satisfactory degree. Moreover it is required not least also against the background of the specific application or use, respectively, provided in each case (for example the use in the defense sector, or in combating emergencies or fires, respectively) in conjunction with the high stress of the material required and associated therewith that the respective protective equipment or clothing has high mechanical stability, for example in terms of preventing premature or excessive, respectively, cracking and delaminating or the like of the underlying material.

It is also to be highlighted in this context that a high level of physical activity or stress, in terms of the respective people is often present, in particular in the use in the defense sector, or in the sector of combating fires or emergencies, respectively, but also in the leisure or sports sector, respectively, particularly in combination with unfavorable service conditions, such as the presence of a high temperature or the like, such that effective wicking of sweat, or an effective exchange of air, respectively, by way of (protective) clothing that is being used has therefore to be guaranteed from the outset. It is also required herein that the materials used to this end provide an ideally comfortable wear experience, so as to enable people equipped with corresponding clothing to be relieved of stress as far as possible from this point of view.

With a view to providing a comprehensive protective concept, it is moreover notable that persons or soldiers, respectively, in particular in military action as well as people active in the context of combating emergencies or fire, respectively, or who often are exposed to the additional risk of contamination by chemical, biological, or radioactive, respectively, harmful and toxic substances. There is generally a high risk potential associated with chemical, biological, and radioactive nuclear toxic substances or warfare agents for people coming into contact with such substances, such as soldiers, firefighters, which are in warfare action or the like, since already minor quantities or concentrations, respectively, of substances of this type can lead to permanent health issues for people confronted with said substances, or even to the death of said people. In this context, it is also relevant that the aforementioned substances can often be present in the form of fine-grain fine-particulate aerosols or the like, or in the form of particles of harmful substance particles present in the (ambient) air, this however representing a great and additional challenge in terms of providing a corresponding protective function, since the aerosols or fine-particulate particles of harmful substances, respectively, in question have correspondingly high penetration properties, for example in terms of air-permeable items of clothing or the like.

In this context, there are a number of substances or materials, which upon contact are received by the skin and lead to severe physical damage already in minor quantities, or concentrations, respectively. In the field of chemical harmful or toxic substances (warfare agents), the vesicant lost (yellow cross) and the nerve agent sarin are to be in particular mentioned to this end. People which may come into contact with such highly toxic poisons therefore have to wear suitable protective clothing, or be protected from said substances by suitable protective materials.

This applies in principle also to biological harmful or toxic substances, respectively, as can likewise be used as warfare agents and which likewise lead to permanent health issues upon contact, and in particular upon direct or indirect contact (i.e. by subsequent absorption into the body, for example by way of mucous membranes or the like). Furthermore, direct contact is also to be avoided with, or contamination by, respectively, radioactive substances, in particular also in the form of radioactive particles or the like.

In order for a certain protective function in relation to the aforementioned harmful and toxic substances to be guaranteed, air-impermeable and water-vapor-impermeable protective suits are known in the prior art, for example, which are equipped with a barrier or rubber layer, respectively, which is impermeable in relation to toxic substances or warfare agents, respectively, in particular of the aforementioned type. The impermeable rubber layer, as a result of the air impermeability, or the impermeability of the membrane, respectively, also leads to a certain protective function in relation to aerosols and particles of harmful substances. Moreover, the rubber layer in question in principle also offers protection in relation to water, also in liquid form, and thus a corresponding protection against rain. However, protective systems of this type are associated with the central disadvantage that clothing, or protective equipment, produced therefrom, for example in the form of protective suits, in the applied or worn state, very rapidly lead to a build-up of heat (for example in the context of combat action with high physical stress for the wearer), since no moisture-regulating and temperature-regulating properties are present by virtue of the absent air-permeability and water-vapor permeability, since neither breathability nor an efficient exchange of air is present. For this reason, protective systems of this type are in principle also not suitable for the sport or leisure sector, respectively, which is associated with high physical activity, since body heat as well as body sweat arising under physical stress cannot be effectively removed by the clothing, as has been set forth above.

Moreover, in the prior art, for example for the production of protective suits, such protective materials which are equipped with an air-impermeable membrane which is however configured so as to be water-vapor-permeable are also used, said membrane being intended to function in particular as a barrier layer in relation to toxic substances. A protective material of this kind is described, for example, in WO 96/37365 A1 as well as in U.S. Pat. No. 5,743,775 A, or DE 195 18 683 A1, the two latter being part of the same pattern family. Protective suits having a membrane which is permeable to water vapor but however is substantially impermeable to toxins, in particular skin toxins, have the fundamental disadvantage that toxins which have invaded at leaking locations which can be caused, for example, by mechanical damage, ingress the interior of the protective suit and can consequently be received through the skin of the wearer. Moreover, the wear comfort by virtue of the overall limited exchange of air is not always satisfactory.

Moreover, air-permeable permeable protective materials which for the purpose of guaranteeing a protective function in relation to harmful and toxic substances can be equipped with an adsorption filter layer based on activated carbon are also known in the prior art for improving in particular the wear comfort. As has been set forth above, protective systems of this type, on account of the increased exchange of air and water, or water vapor, respectively, have an improved wear comfort with a fundamentally positive protective function in relation to toxic or harmful substances, since one advantage lies in that the activated carbon optionally used is also accessible on the internal side, that is on this side of the protective material that faces the wearer, such that toxins which have invaded at damaged locations or otherwise leaking locations can be rapidly adsorbed and rendered harmless. The air-permeable permeable protective suits which act in an adsorptive manner thus have a generally positive protective effect, the latter however not always satisfactory when the toxic substances are present in the form of aerosols and particles of harmful substances. In principle, the air-permeable systems in question per se also have an improved suitability with a view to a use in the sports or leisure sector, respectively. However, the wear comfort can be impeded by virtue of a non-optimal wear experience since the materials in question do not always have optimum material properties, for example in terms of the capability of said materials in terms of flexing and elongating, as well as the snug fit of said materials, such that the wear experience associated therewith is thus correspondingly influence. Moreover, the wind-repelling properties and the protection of materials of this type against wetness is not always optimal, this potentially leading to the wearer suffering hypothermia in such protective clothing under given conditions (heavy wind, rainfall, etc.). Consequently, the materials in question also do not always have optimal thermal conditioning or climate conditioning, respectively.

BRIEF SUMMARY OF THE INVENTION

Summarizing, it is thus to be established that the protective materials or filter materials, respectively, which are known in the prior art and which can in particular be used for producing protective clothing or protective equipment, respectively, do not always have optimal material properties, and in particular material properties which also take into account the respective specific application or use, with a view to guaranteeing a high degree of wear comfort, on the one hand, while at the same time providing a high level of protective function, on the other hand.

Against this background, the object of the present invention thus lies in providing a sheet filter material, or a protective filter material, respectively, which at least largely avoids or at least mitigates the disadvantages of the prior art described above. Such a sheet filter material or protective material, respectively, is in particular intended to be suitable for numerous applications in the sector of textile technology or apparel technology, respectively, for example for the production of protective equipment or protective items, respectively, having a protective function in relation to chemical or biological or radioactive, respectively, harmful or toxic substances, respectively, as well as of clothing or equipment, respectively, for the sports or leisure sector, respectively. Moreover, the features according to the invention is intended to be suitable for the production of filters and filter materials.

A further object of the present invention moreover lies in providing in particular a sheet filter material or protective material, respectively, which provides an effective protective function in relation to chemical, biological, or radioactive, respectively, harmful and toxic substances, having moreover protection in relation to corresponding harmful particles and/or aerosols. In this context, a corresponding sheet filter material having integrated protection in relation to particles or aerosols, respectively, is in particular to be provided.

An even further object of the present invention is moreover also to be seen in providing a corresponding sheet filter material or protective material, respectively, which offers improved wear comfort, in particular with a view to providing positive thermal or climatic conditioning in the applied or worn state, respectively (for example in terms of protective suits or clothing for the sports or leisure sector, respectively, which are produced from the material). In this context, effective wicking of moisture or body sweat, respectively, as well as wind-repellent properties are to be provided with an overall high permeability to water vapor or air. Moreover, the material should have a certain level of protection in relation to wetness.

An even further object of the present invention is moreover to be seen in providing a corresponding sheet filter material or protective material, respectively, which is particularly suitable for use in protective equipment or protective items, respectively, or clothing for the sports or leisure sector, respectively, wherein the material is to guarantee a high level of wear comfort with a view to a wear experience which is improved in relation to the prior art.

Finally, a yet again further object of the present invention lies in providing a sheet filter material or protective material, respectively, which is in particular suitable also for use in filters and filter materials (such as, for example, for removing harmful substances, odorous substances, and toxic substances of all manner, in particular from air flows or gas flows, respectively, such as protection mask filters, odor filters, sheet filters, air filters, room filters, and filters for the medical sector), and herein guaranteeing a positive filter efficiency for the medium to be purified along with a positive flow capability, and specifically also with a view to an effective removal of particles or aerosols, respectively, which are present in the medium to be purified.

Moreover, the sheet filter material or protective material respectively, provided according to the invention is to have a high degree of durability and mechanical stability, and moreover have an optimized or low, respectively, area weight. In the case of the use in or as protective clothing, respectively, the wear properties, or the wear comfort, respectively, is moreover to be improved with a view to the wear experience, or the snug fit, respectively, of the underlying material.

In order for the object described above to be achieved, the present invention, according to a first aspect of the present invention, thus proposes a sheet filter material, in particular having an aerosol or particle filter function, respectively, preferably having a protective function in relation to chemical, biological, and/or radioactive harmful or toxic substances, respectively; respective advantageous refinements and design embodiments of this aspect of the invention are the subject matter of the disclosure.

A further subject matter of the present invention, according to a second aspect of the present invention, is moreover a method for producing the sheet filter material according to the invention. Further advantageous design embodiments of the method according to the invention are the subject matter of the further disclosure.

A further subject matter of the present invention, according to a third aspect of the present invention, is moreover the use of the sheet filter material according to the invention for producing protective equipment or protective items, respectively, of all manner, or for producing sports or leisure wear, respectively, and/or sports or leisure equipment, respectively, or for producing filters and filter materials of all manner, respectively.

A further subject matter of the present invention, according to a fourth aspect of the present invention, relating to the protective equipment or protective items, respectively, according to the invention as well as to the sports and/or leisure wear or sports and/or leisure equipment, respectively, according to the invention, are moreover the protective equipment or protective items, respectively, according to the invention, or the sports and/or leisure wear or sports and/or leisure equipment, respectively, according to the invention, which contain the sheet filter material according to the invention or are produced while using the sheet filter material according to the invention, respectively.

Finally, a further subject of the present invention, according to a fifth aspect of the present invention, relating to filter or filter materials, respectively, are also filter and filter materials which comprise the sheet filter material according to the invention, or are produced while using the sheet filter material according to the invention, respectively.

It goes without saying that in the description hereunder of the present invention those design embodiments, embodiments, advantages, exemplars, or the like which hereunder for the purpose of avoiding unnecessary repetitions are set forth only in the context of a single aspect of the invention of course do also apply in an analogous manner to the other aspects of the invention, without this requiring any explicit mention.

It furthermore goes without saying that the respective indications of values, numbers, and ranges in the indications of values, numbers and ranges hereunder are not to be understood as limiting; it is self-evident to the person skilled in the art that the stated ranges or indications, respectively, may be deviated from in the individual case or application without departing from the scope of the present invention.

It moreover applies that all indications of values or parameters, respectively, or the like, mentioned hereunder can be established or determined in principle, respectively, by normalized standardized or explicitly stated determination methods, or else be established or determined, respectively, with determination or measuring methods, respectively, which are familiar to the person skilled in the art in this field. Unless otherwise stated, the underlying values or parameters, respectively, are determined at standard conditions (i.e. in particular at a temperature of 20° C. and/or at a pressure of 1,031.25 hPa, or 1.01325 bar, respectively).

It moreover applies that it is to be noted in the case of all indications of relative or percentage-wise quantities, in particular weight-related quantities, set forth hereunder that said indications in the context of the present invention are to be selected or combined, respectively, by the person skilled in the art in such a manner that a sum of 100% or 100% by weight, respectively, results at all times, optionally while including further components or ingredients, in particular as defined hereunder. However, this is self-evident to the person skilled in the art.

With the above having been pre-established, the present invention will be described and explained in more detail hereunder, and specifically also by means of drawings or figurative illustrations, respectively, illustrating preferred embodiments or exemplary embodiments, respectively.

DETAILED DESCRIPTION OF THE INVENTION

Figure 1:
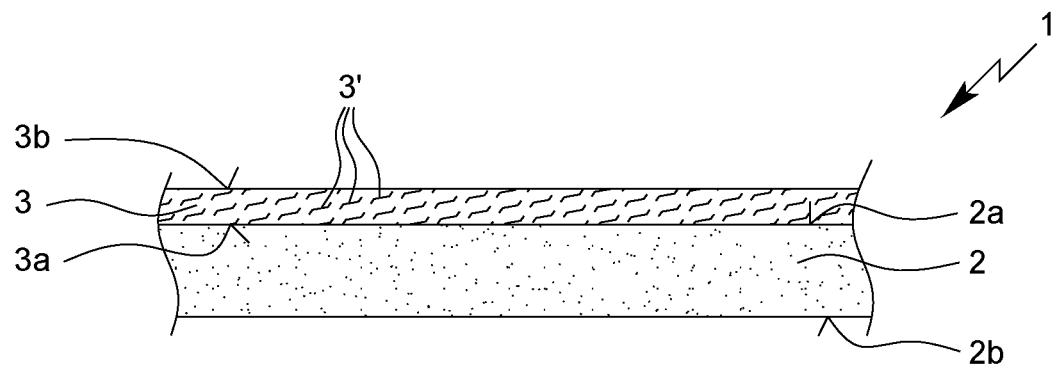
FIG. 1 shows a schematic cross-sectional illustration of a sheet filter material according to the invention, wherein the sheet filter material has an air-permeable or water-vapor-permeable, respectively, foam-based or foam-shaped, respectively, support material, as well as an air-permeable or water-vapor-permeable, respectively, nanofiber layer which is assigned to the support material, or is fixed to, or brought to bond with, a (first) side, in particular flat side, of the support material.

A subject matter of the present invention, according to a first aspect of the present invention, is thus a sheet filter material (synonymously also referred to as a protective material), in particular having an aerosol or particle filter function, respectively, preferably having a protective function in relation to chemical, biological, or radioactive (nuclear), respectively, harmful and toxic substances, wherein the sheet filter material comprises:
(a) an air-permeable and/or water-vapor-permeable, preferably planar, foam-based and/or foam-shaped support material having two mutually opposite sides, in particular flat sides; and
(b) an air-permeable and/or water-vapor-permeable, preferably planar, nanofiber layer, in particular an aerosol and/or particle filter nanofiber layer, which is assigned to the foam-based and/or foam-shaped support material and/or is fixed and/or brought to bond with a (first) side, in particular flat side, of the foam-based and/or foam-shaped support material, wherein the nanofiber layer comprises a multiplicity of nanofibers, or is composed thereof.

According to the invention, a special sheet filter material, or protective material, respectively, is relied on, which has a nanofiber layer which is in particular applied immediately or directly, respectively, to an air-permeable or water-vapor-permeable, respectively, foam-based or foam-shaped, respectively, support material, wherein the nanofiber layer comprises a multiplicity of nanofibers, or is composed thereof, respectively.

According to the invention, it can in particular be provided, as will yet be set forth hereunder, that the sheet filter material according to the invention as a layer (c) moreover has at least one textile carrier which is disposed in particular on the side of the foam-based or foam-shaped, respectively, support material that faces away from the nanofiber layer, and to which in turn the foam-based or foam-shaped, respectively, support material is applied. According to the invention, this can accordingly likewise be a textile sheet filter material or a textile protective material, respectively.

In the context of the present invention, on account of the targeted combination of an air-permeable or water-vapor-permeable, respectively, foam-based or foam-shaped, respectively, support material and a nanofiber layer which is applied thereto, or fixed thereto, respectively, a sheet filter material which at a high air-permeability or water-vapor-permeability, respectively, has an effective protective function in relation to chemical, biological, or radioactive, respectively, harmful or toxic substances is overall provided, wherein the sheet filter material according to the invention in this context has in particular an integrated aerosol or particle filter function, respectively, or a respective protective function also in relation to aerosols and particles, respectively, so to speak.

In this context, the applicant has in an entirely surprising manner established that an efficient protective function in relation to the harmful or toxic substances, respectively, in question, in particular chemical warfare agents, can be provided while simultaneously providing a high air-permeability or water-vapor-permeability, respectively, in that a special layered structure, or a special layered construction, is provided in an expedient manner in terms of the sheet filter material according to the invention, according to which, as has been set forth above, specifically a nanofiber layer comprising a multiplicity of nanofibers, or composed thereof, respectively, is applied or fixed to, respectively, an air-permeable or water-vapor-permeable, respectively, foam-based or foam-shaped, respectively, support material, this as a result leading to outstanding aerosol and particle filter properties.

The applicant herein has found in a likewise surprising manner that in terms of the sheet filter material according to the invention, in particular configured in a layered manner, the respective filter properties of the nanofiber layer, on the one hand, and of the foam-based or foam-shaped, respectively, support material, on the other hand, are mutually complementary, wherein in this context the overall protective function provided by the sheet filter material according to the invention in relation to the harmful or toxic substances, respectively, in question goes beyond the sum of the filter properties of the respective individual components or layers, respectively, such that in terms of the aerosol or particle filter function, respectively, provided according to the invention a synergistic interaction of the respective layers in the form of the nanofiber layer, on the one hand, and of the foam-based or foam-shaped, respectively, support material, on the other hand, is present. In the absence of any intention of being delimited or fixed to this theory in this context, the expedient use of the air-permeable or water-vapor-permeable, respectively, foam-based or foam-shaped, respectively, support material overall also leads to an improved incident flow onto, or passing flow through, respectively, of the nanofiber layer fixed to said support material by way of the medium, in particular air, to be purified and thus also to an optimized utilization of the aerosol or particle filter function provided by the nanofiber layer, wherein according to the invention it may also be that the foam-based or foam-shaped, respectively, support material configured so as to be air-permeable or water-vapor-permeable, respectively, has an additional or independent, respectively, aerosol or particle filter function, respectively.

As a result, aerosols or particles, respectively, which are present in a medium, in particular air, be purified can thus be received by the sheet filter material according to the invention to a high degree, this being associated with a correspondingly high purification of the medium, in particular air, to be purified.

In this regard, the concept according to the invention according to which it is in particular specifically provided to attach the nanofiber layer immediately or directly, respectively, (i.e. without intervening further layers, or without intervening dissimilar materials or components, respectively, such as, for example, adsorption materials) to the air-permeable or water-vapor-permeable, respectively, foam-based or foam-shaped, respectively, support material, or to fix said nanofiber layer thereto, respectively, is awarded high importance, since an optimal effective reinforcement of the respective layers is guaranteed on account thereof, specifically also in terms of the improved incident flow behavior, or passing flow behavior, respectively, of the nanofiber layer containing a multiplicity of nanofibers.

As a result of the targeted interaction of the layers in question, in the form of the air-permeable or water-vapor-permeable, respectively, foam-based or foam-shaped, respectively, support material, on the one hand, and the nanofiber layer, on the other hand, the overall material thickness in terms of the sheet filter material according to the invention can be reduced, this being overall beneficial also in terms of the air-permeability or water-vapor-permeability, respectively, or breathability, respectively, as well as the resulting area weight. Based thereon, the wear properties, or the wear comfort, respectively, of items of clothing or items of equipment, respectively, produced from the sheet filter material are also improved. Moreover, the sheet filter material according to the invention, in particular in terms of the use thereof for (protective) items of clothing is associated with a high degree of wear comfort, specifically with a view of an efficient thermal or climatic conditioning, respectively, being enabled not least by virtue of the high air-permeability or water-vapor-permeability, respectively, or breathability, of the material, for example since moisture or body sweat, respectively, can be efficiently removed or wicked, respectively, from a wearer of corresponding (protective) items of clothing. By virtue of the special configuration of the sheet filter material according to the invention, a high level of wind protection, or wind-repellent properties, respectively, are provided herein despite the high air-permeability, this further improving the wear comfort in particular in terms of the underlying thermal or climatic conditioning, respectively. Hypothermia is in particular counteracted in this manner, for example at very low ambient temperatures, or at strong winds.

According to the invention it is in particular provided that the sheet filter material according to the invention is in particular present as a layer-type or layer-shaped, respectively, composite material, or that the sheet filter material is configured so as to be self-supporting. The sheet filter material according to the invention is highly robust and has a high resistance to abrasion also as a result thereof.

Moreover, an outstanding wear experience, for example when wearing (protective) clothing produced therefrom or therewith, respectively, moreover results by virtue of the special materials or components, respectively, of the sheet filter material according to the invention. The sheet filter material according to the invention herein, at a low area weight, also has outstanding properties in terms of the flexibility or the flexing behavior, respectively, thereof, and specifically also because the foam-based or foam-shaped, respectively, support material, per se is in particular also configured so as to be flexible or reversibly elongatable (elastic), this in principle also applies to the nanofiber layer per se which is provided according to the invention. Moreover, the nanofiber layer which is in particular present in the form of a non-woven as well as the foam-based or foam-shaped, respectively, support material, and thus the sheet filter material according to the invention overall, has a very snug fit, and by virtue of the respective structure of the nanofiber layer, or of the support material, respectively, also has correspondingly positive haptic properties, this further improving the wear comfort.

The sheet filter material according to the invention moreover also has water-proof or water-repellent, respectively, properties, in particular since the special nanofiber layer or the support material, respectively, represents a barrier in relation to water in liquid form, such that the sheet filter material according to the invention in addition to the further properties also provides or has, respectively, a certain protection in terms of water or rain, respectively, or a defined water-proofing, or a defined water-repellent behavior (for example a water column of at least 500 mm, measured according to DIN EN 20 811:1992 (August 1992)). In this context, the material according to the invention can be used, for example, for water-repellent (i.e. repelling water in liquid form), but breathable (i.e. water-vapor-permeable and preferably also air-permeable) protective equipment, sports or leisure wear, respectively, or sports or leisure equipment, respectively, or the like, in particular also for shoe materials or footwear.

The sheet filter material according to the invention can be universally used by virtue of the underlying properties of the sheet filter material according to the invention. Thus for example apart for the use in the context of ABC protection, or NBC protection (nuclear, biological, chemical), a use in the sports or leisure sector, respectively, is also to be considered, also in particular as a result of the high level of wear comfort together with the provided air-permeability and water-vapor-permeability and simultaneously a high protection in relation to wind and protection in relation to water in liquid form, as has been set forth above. Moreover, the sheet filter material according to the invention is suitable for filter applications, for example for room air filters or the like.

In the context of the present invention, a sheet filter material having high air-permeability or water-vapor-permeability is thus provided overall, said sheet filter material by virtue of the outstanding protective function thereof in relation to harmful or toxic substances, respectively, as a result of an aerosol or particle filter function, respectively, provided in this regard being suitable for the use in the field of ABC protection or NBC protection, respectively, where in a use in the sports or leisure sector, respectively, in particular for producing sports or leisure wear, respectively, or sports or leisure equipment, respectively, is moreover expedient, not least by virtue of the underlying wind protection and wetness protection of the material.

The protective function of the sheet filter material according to the invention in relation to particles and aerosols is comparable with that of conventional membrane systems; however, by virtue of the air-permeability or water-vapor-permeability, respectively, of the sheet filter material according to the invention, when said sheet filter material is processed into ABC protective suits or the like the wear comfort is significantly increased in comparison to such protective suits which have a membrane.

Insofar as the present invention is further concerned, the planar nanofiber layer provided is in particular distinguished by the use or the presence, respectively, of a multiplicity of nanofibers. In this context, the term "nanofibers" as used according to the invention, is to be widely interpreted in the context of the present invention. The term in question relates in particular to special fibers which are distinguished by the properties which are yet to be set forth or defined, respectively, hereunder, specifically in particular with a view to special fiber diameters, special materials, as well as the underlying production of the nanofibers. To this end, reference can be made to the explanations hereunder.

The present invention will be described hereunder by means of drawings or figurative illustrations, respectively, which illustrate preferred embodiments or embodiments, respectively, wherein the respective explanations apply to all of the aspects according to the invention, and wherein the corresponding preferred embodiments are not at all limiting.

Figure 2:
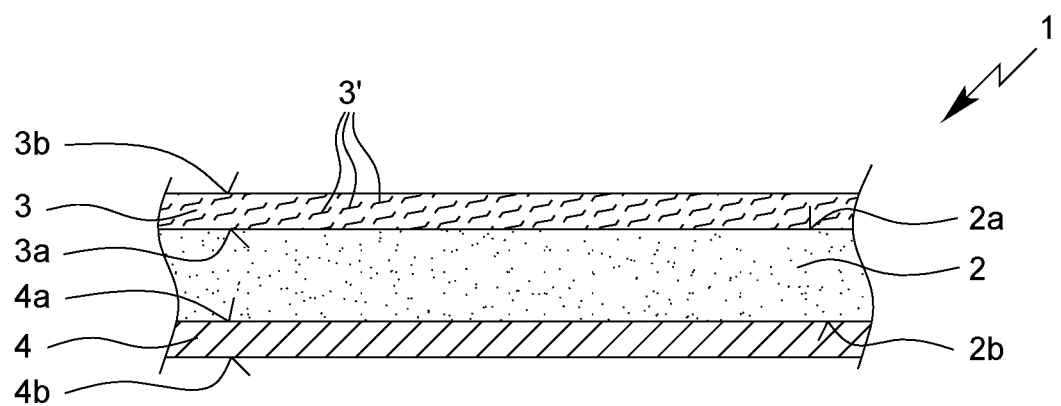
FIG. 2 shows a cross-sectional illustration of a sheet filter material according to the invention according to an embodiment according to the invention, according to which the sheet filter material additionally has a textile carrier which is in particular disposed on the side of the foam-based or foam-shaped, respectively, support material that faces away from the nanofiber layer.
Figure 3:
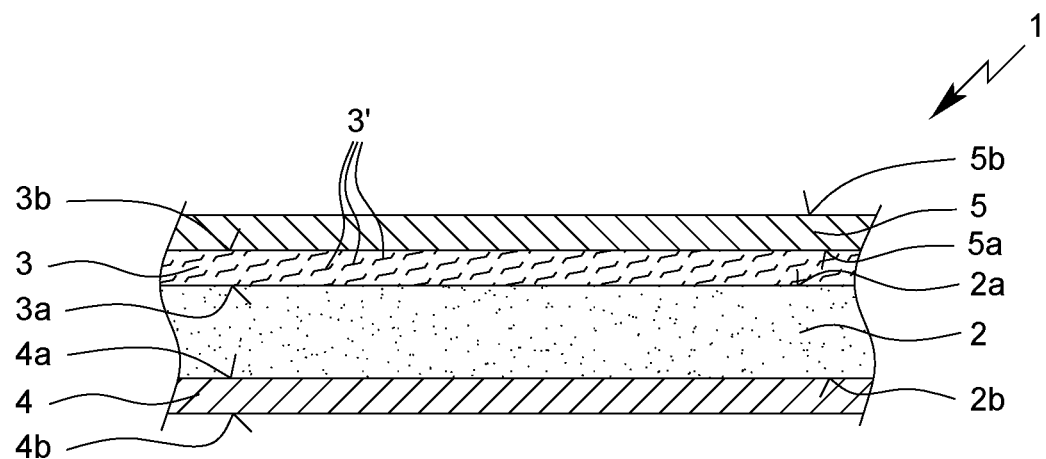
FIG. 3 shows a cross-sectional illustration of a sheet filter material according to the invention, according to a further embodiment of the present invention, according to which the sheet filter material, apart from the foam-based or foam-shaped, respectively, support material and the nanofiber layer as well as the textile carrier, has an additional covering layer which is in particular disposed on the side of the nanofiber layer that faces away from the foam-based or foam-shaped, respectively, support material.
Figure 4:
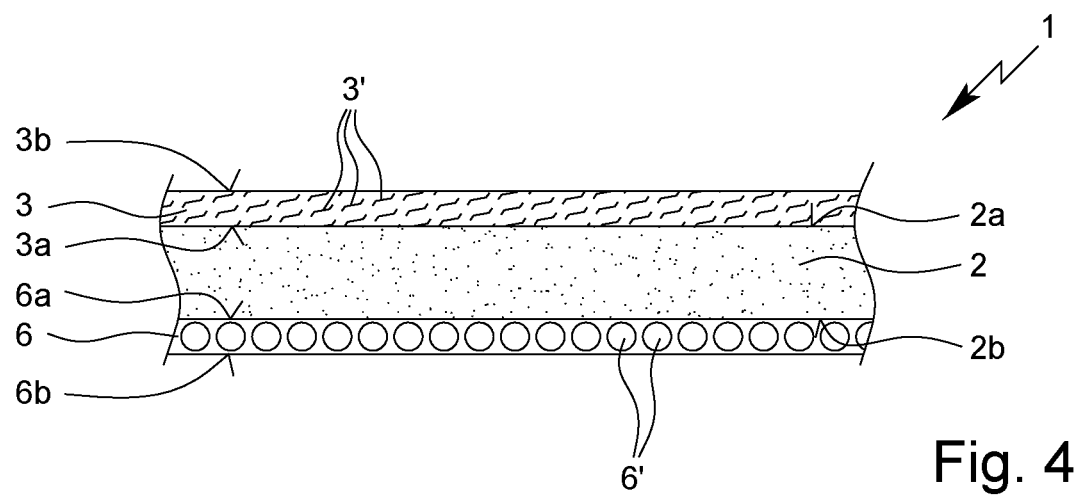
FIG. 4 shows a cross-sectional illustration of a sheet filter material according to the invention, according to yet again a further embodiment of the present invention, according to which the sheet filter material is additionally provided with an adsorption layer, in particular wherein the adsorption layer is disposed on the side of the foam-based or foam-shaped, respectively, support material that faces away from the nanofiber layer.

In the figurative illustrations:

FIG. 1 shows a schematic cross-sectional illustration of a sheet filter material according to the invention, wherein the sheet filter material has an air-permeable or water-vapor-permeable, respectively, foam-based or foam-shaped, respectively, support material, as well as an air-permeable or water-vapor-permeable, respectively, nanofiber layer which is assigned to the support material, or is fixed to, or brought to bond with, a (first) side, in particular flat side, of the support material;

FIG. 2 shows a cross-sectional illustration of a sheet filter material according to the invention according to an embodiment according to the invention, according to which the sheet filter material additionally has a textile carrier which is in particular disposed on the side of the foam-based or foam-shaped, respectively, support material that faces away from the nanofiber layer;

FIG. 3 shows a cross-sectional illustration of a sheet filter material according to the invention, according to a further embodiment of the present invention, according to which the sheet filter material, apart from the foam-based or foam-shaped, respectively, support material and the nanofiber layer as well as the textile carrier, has an additional covering layer which is in particular disposed on the side of the nanofiber layer that faces away from the foam-based or foam-shaped, respectively, support material; and FIG. 4 shows a cross-sectional illustration of a sheet filter material according to the invention, according to yet again a further embodiment of the present invention, according to which the sheet filter material is additionally provided with an adsorption layer, in particular wherein the adsorption layer is disposed on the side of the foam-based or foam-shaped, respectively, support material that faces away from the nanofiber layer.

The figurative illustrations according to FIGS. 1 to 4 which relate to the present invention herein highlight in particular also the first aspect of the present invention, according to which a sheet filter material 1, in particular having an aerosol or particle filter function, respectively, preferably having a protective function in relation to chemical, biological and/or radioactive harmful or toxic substances, is specifically provided, wherein the sheet filter material 1 comprises:

(a) an air-permeable and/or water-vapor-permeable, preferably planar, foam-based and/or foam-shaped support material 2 having two mutually opposite sides 2a, 2b, in particular flat sides; and (b) an air-permeable and/or water-vapor-permeable, preferably planar, nanofiber layer 3, in particular an aerosol and/or particle filter nanofiber layer, which is assigned to the foam-based and/or foam-shaped support material 2 and/or is fixed and/or brought to bond with a (first) side 2a, in particular flat side, of the foam-based and/or foam-shaped support material 2, wherein the nanofiber layer 3 comprises a multiplicity of nanofibers 3', or is composed thereof.

As has been set forth above, in the context of the present invention a sheet filter material is overall provided which unifies the diametrically opposed properties of a high level of wear comfort, which is guaranteed in particular as a result of a high air-permeability and/or water-vapor-permeability, on the one hand, and a high protective function in relation to harmful or toxic substances, respectively, in particular warfare agents, on the other hand, and in one the same material, wherein the sheet filter material according to the invention by virtue of the special properties thereof moreover has an outstanding wear experience and at the same time a positive climate-related or temperature-related conditioning, respectively in particular in the case of said sheet filter material being used in or as a (protective) clothing or the like. The special properties and advantages of the sheet filter material according to the invention herein result from the concept according to the invention according to which an overall air-permeable or water-vapor-permeable, respectively, layer-type or layer-shaped, respectively, sheet filter material is expediently provided based on a special combination of a foam-based or foam-shaped, respectively, support material and a special nanofiber layer.

In this context, it is in particular provided in the context of the present invention that the support material 2 is configured as a foam-based and/or foam-shaped support material, in particular comprises a foam structure (foam layer), preferably a polymer foam structure (polymer foam layer), or is composed thereof.

In this regard, it can be in particular provided according to the invention that the support material 2 is configured so as to be open-pored (synonymously also referred to as an open-cell support material), or open-pored (synonymously also referred to as an open-cell support material). This contributes in particular toward the air-permeability or water-vapor-permeability, respectively, of the support material 2 in question, and moreover also leads to the incident flow behavior or passing flow behavior, respectively, of the nanofiber layer 3 applied to the support material 2 being further improved.

The support material 2 can generally be configured as an open-pored foam-based and/or open-pored foam-shaped support material, in particular comprise an open-pored foam structure (open-pored foam layer), preferably an open-pored polymer foam structure (open-pored polymer foam layer), or be composed thereof.

It can furthermore be provided according to the invention that the support material 2 has an area weight in the range from 5 g/m² to 500 g/m², in particular in the range from 10 g/m² to 300 g/m², preferably in the range from 15 g/m² to 200 g/m², preferably in the range from 20 g/m² to 150 g/m², particularly preferably in the range from 25 g/m² to 100 g/m², most particularly preferably in the range from 25 g/m² to 50 g/m².

The support material 2 can in particular have a thickness of at most 10 mm, in particular at most 5 mm, preferably at most 4 mm, preferably at most 3 mm, particularly preferably at most 1 mm, most particularly preferably at most 0.5 mm. The support material 2 can in particular have a thickness in the range from 0.01 mm to 10 mm, in particular in the range from 0.03 mm to 5 mm, preferably in the range from 0.05 mm to 4 mm, preferably in the range from 0.08 mm to 3 mm, particular preferably in the range from 0.09 mm to 1 mm, most particular preferably in the range from 0.1 mm to 0.5 mm, furthermore preferably in the range from 0.1 mm to 0.3 mm. In this context, the term of the thickness of the support material 2 is in particular understood to be the spacing of the (first) side 2a from the (second) side 2b of the support material 2.

It can in particular be provided according to the invention that the support material 2 has a density in the range from 50 g/l to 500 g/l, in particular in the range from 100 g/l to 400 g/l, preferably in the range from 150 g/l to 350 g/l, preferably in the range from 200 g/l to 325 g/l.

As has been set forth above, the support material 2 used according to the invention is distinguished by a high air-permeability, this in turn improving the incident flow behavior or passing flow behavior, respectively, in terms of the nanofiber layer 3 used according to the invention. It can in particular be provided according to the invention that the support material 2 has an air permeability of at least 100 $l \cdot m^{-2} \cdot s^{-1}$, in particular at least 200 $l \cdot m^{-2} \cdot s^{-1}$, preferably at least 300 $l \cdot m^{-2} \cdot s^{-1}$, particularly preferably at least 400 $l \cdot m^{-2} \cdot s^{-1}$, most particularly preferably at least 600 $l \cdot m^{-2} \cdot s^{-1}$, at a flow resistance of 127 Pa.

Foam structures which are particularly stable or capable of mechanical stress, respectively, and in particular are reversibly elongatable, are obtained according to the invention when the support material 2, in particular the foam structure, preferably the polymer foam structure, comprises a material or a foam structure material, respectively, (i.e. a material forming the support material 2, in particular the foam structure, preferably the polymer foam structure, synonymously also referred to as the foam structure polymer) or a compound from the group of polyacrylate (PAC), poly methyl acrylate (PMA), polymethyl methyl acrylate (PMMA), polycarbonate (PC), polyurethane (PUR) and silicones as well as mixtures or combinations of at least two of the aforementioned materials and/or compounds, preferably polyurethane (PUR), or is formed therefrom, respectively. In other words, it can be provided according to the invention that the support material 2, in particular the foam structure, preferably the polymer foam structure, comprises polyacrylate (PAC), poly methyl acrylate (PMA), polymethyl methyl acrylate (PMMA), polycarbonate (PC), polyurethane (PUR) or silicone, respectively, preferably polyurethane (PUR), or is formed therefrom.

According to one embodiment according to the invention it can be provided in particular that the support material 2, in particular the foam structure, preferably the polymer foam structure, is configured as an open-pored polyurethane foam structure. The foam structure used according to the invention is generally and in particular a dried or cured, respectively, preferably cross-linked foam structure, in particular polymer foam structure.

A foam-based or foam-shaped, respectively, (carrier) material according to the invention is generally understood to be an in particular firm (i.e. dried or cured, respectively, preferably cross-linked) but flexible or flexural or reversibly compressible or reversibly elongatable, respectively, foam structure (foam layer), or a firm porous body, respectively, i.e. in particular based on a dispersion with a solid substance as the dispersion medium and a gas as a dispersed phase. Formations from gas-filled, in particular air-filled, pores or cells, respectively, which are in particular delimited by firm cell webs or lamellae, respectively, are generally understood to be firm foam structures or foams, respectively. The cell webs or lamellae, respectively, which are based on a material underlying the foam structure and which are connected as nodes, so to speak, herein form a contiguous framework. In other words, an overall porous structure is created on account of the gas-filled or air-filled, respectively, cells within the cell webs or lamellae, respectively. When the cell webs or lamellae, respectively, are configured only incompletely or interrupted, respectively, an open-cell or open-pored, respectively, foam structure is created such as can be used in the context of the present invention according to one embodiment according to the invention. It is particularly advantageous in open-cell or open-pore, respectively, foam structures or foam systems, respectively, that the latter are particularly well accessible to the fluid media to be purified and there are generally hardly any pressure losses. In the context of the present invention it is also guaranteed here in that the nanofiber layer attached to the carrier layer is better accessible for particles or aerosols, respectively, to be removed, as has been set forth above. For further details relating to the term "foam", reference can in particular be made to Römpp, Chemielexikon, 10th edition, Georg Thieme Publishers, Stuttgart/New York, keyword: "Schaum" ("foam"), pages 3950 and 3951 as well as the literature cited therein, the entire content in this regard herewith being fully incorporated by reference.

According to one embodiment of the invention it can in particular be provided that the support material 2, in particular the foam-based and/or foam-shaped support material, comprises or is composed of an in particular dried and/or cured, preferably cross-linked, broken foam structure (synonymously also referred to as a broken foam layer or a broken foam, respectively), in particular a broken polymer foam structure (synonymously also referred to as a broken polymer foam layer or broken polymer foam, respectively). In other words, it can in particular be provided according to the invention that a broken foam structure, in particular a broken polymer foam structure is used as the support material 2, in particular on the basis of the foam-based and/or foam-shaped support material. In this context, the support material 2, in particular the foam-based and/or foam-shaped support material, can thus be an air-permeable and/or discontinuously configured layer based on, or in the form of, respectively, and in particular dried or cured, respectively, preferably cross-linked, broken foam structure, in particular a broken polymer foam structure.

According to the present invention, the foam-based or foam-shaped, respectively, support material 2 can thus in particular be present as a broken foam structure or polymer foam structure, respectively. In the context of the present invention, the term "broken" (synonymously also referred to as "disintegrated" or "destroyed", respectively), such as is used with reference to the dried or cured, respectively, in particular cross-linked, foam structure or polymer foam structure, respectively, or the foam-based or foam-shaped, respectively, support material per se, according to the present embodiment, is in particular to be understood such that the broken foam structure, in particular the polymer foam structure, in the context of the present invention is likewise an overall air-permeable system which, in particular as the result of a special method management for producing the material, proceeding from a previously foamed, not dried, dispersion or solution, which can be applied, for example, to a textile carrier 4 or a removable carrier layer as defined hereunder, respectively, wherein breaking or destroying, respectively, the foam structures can take place upon completed drying or curing, respectively, in the dried or cured, respectively, state has a multiplicity of destroyed or burst or collapsed, respectively, foam bubbles. Accordingly, in terms of the dried or cured, respectively, in particular cross-linked, broken foam structure, in particular polymer foam structure, or of the foam-based or foam-shaped, respectively, support material 2, respectively, reference can also be made to a disintegrated foam structure (disintegrated foam). The broken foam structure, or the underlying destroyed foam bubbles, respectively, herein has/have a multiplicity of destroyed or broken or collapsed, respectively, walls, lamellae or webs, respectively, from the underlying material of the foam structure, in particular the polymer material, in particular as has been defined above. It is in particular moreover the case herein that the foam structure thus obtained is likewise flexible or flexural, respectively, as well as reversibly compressible or reversibly elongatable, respectively.

Moreover, a multiplicity of breakthroughs, pores, ducts or openings, respectively, results in the underlying foam system of the support material 2 as a result of the open-pored foam structure, or of the destroyed or broken or disintegrated, respectively, foam structure, said breakthroughs, pores, ducts or openings, respectively, continuing in particular through the entire layer thickness of the support material 2, which leads overall to the improved air-permeability of the support material 2 which is created in the context of the breaking or the disintegration, respectively, of the foam structure or of the open-pored characteristic of the foam structure, respectively.

It is in particular the case according to the invention herein that the support material 2, in particular the broken foam structure, preferably the broken polymer foam structure, has a multiplicity of dried and/or cured, in particular cross-linked, destroyed and/or burst or collapsed, respectively, foam bubbles.

In this context, it can be provided according to the invention that the support material 2, in particular the broken foam structure, preferably the broken polymer foam structure, preferably the dried and/or cured, in particular cross-linked, destroyed and/or burst and/or collapsed foam bubbles of the support material 2, in particular of the broken foam structure, preferably of the broken polymer foam structure, has/have a multiplicity of destroyed and/or broken and/or collapsed walls and/or webs, in particular from foam structure material (foam structure polymer).

It can in particular be provided according to the invention that the support material 2, in particular the broken foam structure, preferably the broken polymer foam structure, has a proportion of destroyed and/or burst and/or collapsed foam bubbles of at least 10%, in particular at least 30%, preferably at least 50%, preferably at least 70%, particularly preferably at least 90%, most particularly preferably at least 95%, in terms of the overall number of foam bubbles in the support material 2, in particular the broken foam structure, preferably the broken polymer foam structure.

According to one embodiment according to the invention it can be moreover provided that the support material 2, in particular the broken foam structure, preferably the broken polymer foam structure, has a proportion of destroyed and/or burst and/or collapsed foam bubbles in the range from 10% to 100%, in particular in the range from 30% to 99.9%, preferably in the range from 50% to 99%, preferably in the range from 70% to 99%, particularly preferably in the range from 90% to 98%, in terms of the overall number of foam bubbles in the support material 2, in particular in the broken foam structure, preferably in the broken polymer foam structure.

In this context it can in particular be provided according to the invention that the support material 2, in particular the broken foam structure, preferably the broken polymer foam structure, is configured so as not to be closed or open-pored, respectively, or that the support material 2, in particular the broken foam structure, preferably the broken polymer foam structure, has a multiplicity of breakthroughs, pores, ducts or openings, respectively, which in particular extend in the support material 2, in particular in the broken foam structure, preferably in the broken polymer foam structure, or has a multiplicity of breakthroughs, pores, ducts and/or openings which in particular connect the respective sides 2a, 2b of the support material 2. On account thereof, the high air-permeability or water-vapor permeability, respectively, of the support material provided according to the invention is furthermore improved.

It can be generally provided according to the invention that the support material 2, in particular the broken foam structure, preferably the broken polymer foam structure, in comparison to a corresponding non-foamed and/or continuously configured support material, in particular in comparison to a corresponding non-foamed and/or continuously configured foam structure material (foam structure polymer), preferably in comparison to a corresponding non-foamed and/or continuously configured foam structure or polymer foam structure, respectively, has a density and/or in particular area-related volumetric weight which are/is reduced by at least 5%, in particular at least 10%, preferably at least 15%, preferably at least 20%, particularly preferably at least 25% in terms of the non-foamed and/or continuously configured support material, in particular in terms of the non-foamed and/or continuously configured foam structure material, preferably in terms of the non-foamed and/or continuously configured foam structure or polymer foam structure, respectively.

The support material 2, in particular the broken foam structure, preferably the broken polymer foam structure, in comparison to a corresponding non-foamed and/or continuously configured support material, in particular in comparison to a corresponding non-foamed and/or continuously configured foam structure material (foam structure polymer), can moreover have a reduced density and/or in particular area-related volumetric weight which are/is reduced in the range from 5% to 80%, in particular in the range from 10% to 70%, preferably in the range from 15% to 60%, preferably in the range from 20% to 55%, in terms of the non-foamed and/or continuously configured support material, in particular in terms of the non-foamed and/or continuously configured foam structure material.

It can furthermore be provided according to the invention that the support material 2, in particular the broken foam structure, preferably the broken polymer foam structure, in comparison to a corresponding non-foamed and/or continuously configured support material, in particular in comparison to a corresponding non-foamed and/or continuously configured foam structure material (foam structure polymer) has a density and/or in particular area-related volumetric weight which are/is increased by at most 10%, in particular at most 5%, preferably at most 1%, in terms of the non-foamed and/or continuously configured support material, in particular in terms of the non-foamed and/or continuously configured foam structure material.

It is moreover possible in the context of the present invention that the support material 2, in particular the broken foam structure, preferably the broken polymer foam structure, in comparison to a corresponding non-foamed and/or continuously configured support material, in particular in comparison to a corresponding non-foamed and/or continuously configured foam structure material (foam structure polymer) has an elasticity and/or reversible elongatability which are/is reduced by at most 30%, in particular at most 20%, preferably at most 10%, preferably at most 5%, in terms of the non-foamed and/or continuously configured support material, in particular in terms of the non-foamed and/or continuously configured foam structure material.

The support material 2, in particular the broken foam structure, preferably the broken polymer foam structure, in comparison to a corresponding non-foamed and/or continuously configured support material, in particular in comparison to a corresponding non-foamed and/or continuously configured foam structure material (foam structure polymer), can likewise have an elasticity and/or reversible elongatability which are/is reduced in the range from 5% to 30%, in particular in the range from 10% to 20%, in terms of the non-foamed and/or continuously configured support material, in particular in terms of the non-foamed and/or continuously configured foam structure material.

It is generally the case in the context of the present invention that the support material 2, in particular the broken foam structure, preferably the broken polymer foam structure, is configured so as to be contiguous or coherent, respectively. On account thereof, high stability or mechanical load-bearing capability, respectively, is achieved also in terms of the sheet filter material according to the invention.

It can in particular be the case according to the invention that the support material 2, in particular the broken foam structure, preferably the broken polymer foam structure, is obtainable by drying and/or curing, in particular cross-linking, of a foamed, preferably foamed while introducing mechanical energy, an aqueous or organic, preferably aqueous, solution and/or dispersion of a foam structure material (foam structure polymer), in particular in association with at least partially breaking the foam or foam structure, respectively, provided by the foamed solution and/or dispersion of the foam structure material.

In this context, the drying or curing, respectively, in particular the cross-linking, can in particular be carried out in the presence of at least one foaming agent and optionally of at least one foam stabilizer and optionally of at least one cross-linking agent and optionally of at least one emulsifier and optionally of at least one thickening agent.

Insofar as the underlying foam structure material is concerned which is used for configuring the foam-based and/or foam-shaped support material 2, in particular the broken foam structure, preferably the broken polymer foam structure, said foam structure material can thus be selected from the group of polyacrylate (PAC), poly methyl acrylate (PMA), polymethyl methyl acrylate (PMMA), polycarbonate (PC), polyurethane (PUR) and silicones as well as mixtures or combinations of at least two of the aforementioned materials and/or compounds, preferably polyurethane (PUR). It is preferred according to the invention herein that the foam structure material comprises a polyurethane (PUR), or is composed thereof, respectively.

The solution or dispersion, respectively, of the foam structure material can generally contain an aqueous or organic, preferably aqueous, initial solution and/or dispersion of the foam structure material. Moreover, the initial solution can contain the foam structure material used for the carrier layer 2 in quantities in the range from 45 parts by weight to 160 parts by weight, in particular in the range from 50 parts by weight to 140 parts by weight, preferably in the range from 70 parts by weight to 120 parts by weight, in terms of the solution or dispersion, respectively, of the foam structure material. Moreover, the initial solution and/or dispersion of the foam structure material can have a solids content, in particular in the form of the foam structure material, in the range from 15% by weight to 90% by weight, in particular in the range from 25% by weight to 80% by weight, preferably in the range from 40% by weight to 65% by weight, in terms of the solution and/or dispersion of the foam structure material.

The solution and/or dispersion of the foam structure material can likewise contain the foaming agent in quantities in the range from 0.3 parts by weight to 10 parts by weight, in particular in the range from 0.6 parts by weight to 5 parts by weight, preferably in the range from 0.8 parts by weight to 1.8 parts by weight, in terms of the solution and/or dispersion of the foam structure material.

Moreover, the foam stabilizer can in particular be an anionic fatty acid salt. The solution or dispersion, respectively, of the foam structure material can in particular contain the foam stabilizer in quantities in the range from 2.5 parts by weight to 25 parts by weight, in particular in the range from 4 parts by weight to 20 parts by weight, preferably in the range from 5 parts by weight to 10 parts by weight, in terms of the solution and/or dispersion of the foam structure material.

It can moreover be provided according to the invention that the cross-linking agent is an in particular blocked isocyanate, preferably an in particular blocked aliphatic poly isocyanate.

The solution or dispersion, respectively, of the foam structure material herein can generally contain the cross-linking agent in quantities in the range from 0.5 parts by weight to 15 parts by weight, in particular in the range from 1 part by weight to 10 parts by weight, preferably in the range from 3 parts by weight to 8 parts by weight, in terms of the solution and/or dispersion of the foam structure material.

The emulsifier can moreover be an in particular non-ionic polyglycol ether, preferably an in particular non-ionic aryl polyglycol ether. The solution or dispersion, respectively, of the foam structure material can in particular contain the emulsifier in quantities in the range from 0.3 parts by weight to 9 parts by weight, in particular in the range from 0.6 parts by weight to 4 parts by weight, preferably in the range from 1.2 parts by weight to 2.5 parts by weight, in terms of the solution and/or dispersion of the foam structure material.

Moreover, the solution or dispersion, respectively, of the foam structure material can contain the thickening agent in quantities in the range from 0.06 parts by weight to 4.5 parts by weight, in particular in the range from 0.12 parts by weight to 3 parts by weight, preferably in the range from 0.25 parts by weight to 1 part by weight, in terms of the solution or dispersion, respectively, of the foam structure material.

In this way, overall particularly high-performance foams with high stability and high air permeability can be obtained for the support material 2.

In so far as the nanofiber layer 3 provided according to the invention is concerned, said nanofiber layer 3 generally has two opposite sides 3*a*, 3*b*, in particular flat sides, as is likewise set forth in FIGS. 1 to 4.

As likewise shown in FIG. 1 to FIG. 4, it is the case according to the invention in particular that the nanofiber layer 3 is fixed to, or brought to bond with, respectively, the (first) side 2*a* of the support material 2 by way of a (first) side 3*a*, in particular a flat side.

It can likewise be derived from FIGS. 1 to 4 in question that the nanofiber layer 3 can be assigned to the support material 2 at least substantially across the entire face and/or the entire side, in particular by way of a (first) side 3*a*, in particular a flat side, of the nanofiber layer 3.

In this context, it can in particular be provided according to the invention that the nanofiber layer 3 is fixed to, or brought to bond with, respectively, the (first) side 2*a* of the support material 2 in particular by way of a (first) side 3*a*, in particular flat side, of the nanofiber layer 3. In this regard, it is in particular achieved according to the invention that the layers in question can interact or cooperate, respectively, in an optimal manner in terms of the air permeability provided according to the invention, or in terms of the aerosol or particle filter function, respectively, underlying the sheet filter material according to the invention. Moreover, a mechanically stable composite is provided on account of the connection of the layers in question at least substantially across the entire face.

According to one preferred embodiment according to the invention it can moreover be provided that the nanofiber layer 3 is assigned immediately and/or directly and/or without (an) intervening layer(s), in particular without an intervening adsorption layer, to the support material 2, in particular by way of a (first) side 3a, preferably a flat side, of the nanofiber layer 3.

The nanofiber layer 3 can consequently be fixed and/or brought to bond immediately or directly or without intervening layers, in particular without an intervening adsorption layer, on the (first) side 2a of the support material 2, in particular by way of a (first) side 3a, preferably a flat side, of the nanofiber layer 3. A connection of the layers in question across in particular the entire face or the entire side, respectively, can thus also be present in this context. To this end, reference can also be made to the figurative illustrations according to FIGS. 1 to 4.

According to the invention, it is in particular the case according to one preferred embodiment in such a way that the nanofiber layer 3 is fixed to and/or brought to bond with the support material 2, in particular on the (first) side 2a of the support material 2 without the use or addition, respectively, of a bonding and/or adhesive bonding agent.

It can in particular be provided according to the invention in this context that the nanofiber layer 3 is fixed to and/or brought to bond with the support material 2, in particular on the (first) side 2a of the support material 2, by means and/or as a result of an inherent adhesiveness of the nanofibers 3' and/or of the support material 2, preferably of the nanofibers 3', said inherent adhesiveness being in particular present in the production of the sheet filter material 1 and/or of the nanofiber layer 3.

The overall weight of the sheet filter material according to the invention can be further reduced by dispensing with further bonding and/or adhesive bonding agents, respectively.

The nanofiber layer 3 can generally be configured as a textile planar formation, in particular a three-dimensional textile planar formation, which comprises the nanofibers 3' and/or is composed thereof. A high level of efficiency in terms of providing the aerosol or particle filter function in question, respectively, is achieved on account thereof.

The nanofibers 3' can in particular be disposed randomly or in a non-oriented manner, respectively, in the nanofiber layer 3. A dense but air-permeable disposal of the nanofibers 3' in the nanofiber layer 3 is guaranteed in this way, this leading to positive aerosol or particle filter properties, respectively.

Moreover, the nanofibers 3' can be connected to one another, in particular permanently connected to one another or adhesively bonded to one another, respectively, in the nanofiber layer 3, in particular by means or as a result of, respectively, an inherent adhesiveness of the nanofibers 3', said inherent adhesiveness being in particular present in the production of the sheet filter material 1 or of the nanofiber layer 3, respectively. Consequently, the use of additional bonding or adhesive agents, respectively, can also be dispensed with from this point of view, as has been set forth above.

It is in particular the case according to the invention that the nanofibers 3' configure a contiguous and/or coherent planar formation, in particular a planar composite material, in the nanofiber layer 3. It is thus in particular the case that the nanofiber layer is configured as a contiguous or coherent, respectively, planar formation, in particular a planar composite material.

It is preferable herein according to the invention that the nanofiber layer 3 is configured as a cross-fabric or a textile composite cloth, in particular a non-woven, preferably as a non-woven, preferably as a random non-woven.

In particular, the nanofiber layer 3, in particular the nanofibers 3' that configure the nanofiber layer 3, can be produced by electrospinning (electrospinning method or electrospinning, respectively), a spun-bonding method, a melt-blow method, or a combination of the aforementioned methods, preferably by electrospinning. Materials having the best results in terms of the aerosol or particle protection, respectively, can unexpectedly be produced or provided on the basis of the previously mentioned method, in particular by electrospinning, while at the same time having a positive air permeability and a low area weight.

The methods underlying the production of the nanofiber layer 3 or the respective nanofibers 3', respectively, are known per se to the person skilled in the art. The method of electrospinning is generally understood to be the production of corresponding nanofibers in particular from polymer solutions and/or dispersions by way of a treatment in an electric field. To this end, one can in particular proceed in such a manner that the polymer solution underlying the nanofibers to be produced is metered at an electrode and is drawn from the electrode and accelerated by an electric field, wherein the polymer solution or dispersion, respectively, is split into small and minute fibers or spun formations, respectively, which subsequently can be deposited on or applied to, respectively, the support material 2 which in this regard can function as a counter electrode.

The obtained nanofiber layer 3 generally has a three-dimensional network of nanofibers 3' which, so to speak, are stacked on top of one another or deposited on top of one another, respectively, and are in particular connected to one another by way of nodes. In this context, a net of mutually interconnected nanofibers is present for the nanofiber layer 3, so to speak, wherein a high porosity and large surface caused by the disposal of structure of the nanofibers 3' results. The nanofiber layer 3 used according to the invention herein is generally distinguished by a minor thickness and a minor area weight. The nanofiber layer 3 herein generally has a high air-permeability or water-vapor permeability, respectively, and a high water tightness, or a highly water-repellent behavior, respectively, wherein wind-repellent and wetness-repellent properties are moreover also present such that the nanofiber layer 3 used according to the invention has a high functionality associated with a correspondingly large usage or application spectrum, respectively, of the sheet filter material 1 according to the invention which comprises the nanofiber layer 3.

The term "non-woven" in the context of the present invention is in particular used as a term for flexible, porous, planar formations which are part of the family of textile composite cloth's and which are not produced by the classic methods of interweaving more and weft or by loop formation, but by interlacing or cohesively or adhesively, respectively, connecting corresponding fibers, presently the nanofibers 3' in question. Non-wovens are generally loose materials from spun fibers or filaments, in particular produced from synthetic fibers or chemical fibers, the cohesion thereof being generally provided by way of the fibers, and of the inherent bonding or adhesive capability, respectively, which is present in particular in the production. The individual fibers herein can have a preferred orientation (so-called oriented or cross-laid non-wovens) or else be non-oriented (so-called random non-wovens, as preferred according to the invention). The non-wovens can be mechanically consolidated, in particular by needle bonding, stitch-bonding, or by entangling by means of sharp water jets (so-called spun-laced non-wovens). Non-wovens or random non-wovens, respectively, which are particularly suitable according to the invention can be produced, for example, by spun-bonding methods, melt-blow methods, and preferably by electrospinning.

For further details relating to the term non-wovens and non-woven cloths reference can be made, for example, to Römpp, Chemie Lexikon, 10th edition, Georg Thieme Publishers, Stuttgart/New York, volume 6, 1999, pages 4889/4890, keyword: "Vliesstoffe" ("non-woven cloths"), the disclosed content in this regard as well as the literature cited therein, herewith being fully incorporated by reference.

The nanofiber layer 3 used according to the invention, or the nanofibers 3' configuring the nanofiber layer 3, respectively, can in particular be produced according to the explanations in U.S. Pat. No. 6,641,773 B2, WO 2016/171327 A1, WO 2016/171326 A1, WO 2015/053443 A1, as well as WO 2008/136581 A1, the disclosed content thereof in this regard herewith being in each case fully incorporated by way of reference.

The nanofiber layer 3 according to the invention can have an area weight in the range from 0.2 g/m² to 60 g/m², in particular in the range from 0.5 g/m² to 40 g/m², preferably in the range from 0.8 g/m² to 20 g/m², preferably in the range from 0.9 g/m² to 10 g/m², particular preferably in the range from 0.95 g/m² to 5 g/m², most particularly preferably in the range from 1 g/m² to 3 g/m². The applicant has surprisingly found that in particular the aerosol or particle protection, respectively, can be effectively improved or optimized, respectively, in this way.

Moreover, the nanofiber layer can have the thickness of at most 100 μm, in particular at most 50 μm, preferably at most 20 μm, preferably at most 10 μm, particularly preferably at most 5 μm. In this context, the nanofiber layer 3 can have a thickness in the range from 0.001 μm to 100 μm, in particular in the range from 0.005 μm to 50 μm, preferably in the range from 0.008 μm to 20 μm, preferably in the range from 0.01 μm to 10 μm, particularly preferably in the range from 0.15 μm to 8 μm, most particular preferably in the range from 1 μm to 7 μm, furthermore preferably in the range from 2 μm to 6 μm, even furthermore preferably in the range from 3 μm to 5 μm, yet again furthermore preferably in the range from 4 μm to 5 μm. In this context, the term of the thickness of the nanofiber layer 3 is in particular understood to be the spacing of the (first) side 3a from the (second) side 3b of the nanofiber layer 3.

The Nanofiber layer 3 can moreover in general have a density in the range from 10 kg/m³ to 1,000 kg/m³, in particular in the range from 100 kg/m³ to 800 kg/m³, preferably in the range from 150 kg/m³ to 500 kg/m³, preferably in the range from 200 kg/m³ to 300 kg/m³.

Moreover, the nanofiber layer 3 can have an air permeability of at least 30 l·m⁻²·s⁻¹, in particular at least 40 l·m⁻²·s⁻¹, preferably at least 50 l·m⁻²·s⁻¹, particularly preferably at least 100 l·m⁻²·s⁻¹, most particularly preferably at least 150 l·m⁻²·s⁻¹, at a flow resistance of 127 Pa.

By virtue of the defined air permeability also of the nanofiber layer 3, the wear comfort of the sheet filter material according to the invention is in particular also increased, this leading to a high suitability of the material for protective equipment such as ABC protective suits, as well as items of clothing for the sports or leisure sector; the wear comfort can in particular be significantly increased in comparison to membrane suits or the like.

Moreover, wind-repellent and wetness-repellent properties are provided in particular on account of the nanofiber layer 3, in particular also when interacting with the carrier layer 2, this again improving the suitability of the material for the aforementioned application purposes.

Insofar as the nanofibers 3' underlying the nanofiber layer are concerned, said nanofibers 3' generally have a fiber diameter in the range from 1 nm to 5,000 nm, in particular in the range from 5 nm to 2,500 nm, preferably in the range from 10 nm to 2,000 nm, preferably in the range from 15 nm to 1,500 nm, particular preferably in the range from 20 nm to 1,000 nm, most particularly preferably in the range from 25 nm to 750 nm, furthermore preferably in the range from 50 nm to 500 nm. The nanofibers 3' can in particular have a mean fiber diameter $D_{50}$ in the range from 2 nm to 4,500 nm, in particular in the range from 10 nm to 2,000 nm, preferably in the range from 15 nm to 1,750 nm, preferably in the range from 20 nm to 1,250 nm, particularly preferably in the range from 25 nm to 750 nm, most particularly preferably in the range from 30 nm to 500 nm, furthermore preferably in the range from 60 nm to 400 nm. Further optimization of the nanofiber layer 3, in particular in terms of the aerosol or particle filter properties, respectively, provided in this regard is present in the presence of the aforementioned fiber diameters.

The aforementioned fiber diameters herein can be determined using methods known per se to the person skilled in the art. In particular, the fiber diameters in question can be determined microscopically, for example while using in particular digital light microscopy, raster electron microscopy (REM) or transmission electron microscopy (TEM), respectively, in particular in each case in conjunction with digital or electronic image evaluation, respectively. The aforementioned fiber diameters can in particular be determined so as to correspond to the explanations according to WO 2015/009962 A1, the disclosure content thereof in this regard being fully incorporated herewith by reference. Moreover, the aforementioned fiber diameters can in particular be determined so as to correspond to the explanations in the publication according to Ziabari et al., "*A New Image Analysis Based Method for Measuring Electrospun Nanofiber Diameter*", Nanoscale Research Letters, December 2007, 2:597.

The nanofiber layer 3 generally has openings or pores that are delimited by the nanofibers 3'. In this context, the nanofiber layer 3 can have a mean opening size or mean pore size of at most 150 μm, in particular at most 100 μm, preferably at most 50 μm, particularly preferably at most 30 μm, most particular preferably at most 20 μm, even more preferably at most 10 μm. Moreover, the ratio of the mean opening size or of the mean pore size, on the one hand, to the mean fiber diameter $D_{50}$ of the nanofibers 3' can be in the range from 0.2 to 1,800, in particular 1 to 400, preferably 5 to 300, particularly preferably 10 to 250, most particularly preferably 25 to 225. The aerosol or particle filter properties, respectively, are also further improved on account thereof, or the properties in this regard can be predefined or tailored, respectively, in a targeted manner, wherein a high air-permeability or water-vapor-permeability is in particular simultaneously guaranteed.

Synthetic fibers (chemical fibers) can generally be used as nanofibers 3'. In particular, the nanofibers 3 can comprise a material and/or a compound from the group of polyesters (PES), polyolefins such as polyethylene (PE), polypropylene (PP), polyoxyethylene and polyoxypropylene; polyvinyl-chlorides (CLF); polyvinylidene chlorides (CLF); acetates (CA); triacetates (CTA); polyacryl (PAN), in particular polaycryl nitriles; polyamides (PA); polyamide imides (PAI); polyether sulfones (PESU); polystyrenes (PS); polyvinyl alcohols (PVAL); polyurethanes, polyvinyl esters; poly(methyl) acrylates; polyvinylidene fluorides (PVDF); viscose (CV); lyocell; silicones; as well as mixtures or combinations of at least two of the aforementioned materials and/or compounds, particularly preferably polyesters, polyolefins, polyamides, polyacryl nitriles, poly(methyl) acrylates, polyamide imides; polyether sulfonides; polystyrenes and polyvinylidene fluorides, as well as mixtures or combinations of at least two of the aforementioned materials and/or compounds, or be composed thereof.

It can likewise be provided according to the invention that fibers based on and/or in the form of at least one biopolymer compound are used as nanofibers 3'. The nanofibers 3' can in particular comprise a material or a compound, respectively, from the group of gelatin, chitosan, collagen, poly aramids (PAA), polylactic acids (PLA), as well as mixtures or combinations of at least two of the aforementioned materials and/or compounds, or are composed thereof.

The aforementioned materials are in particular associated with high stability and the defined configuration of the nanofibers 3', or the nanofiber layer 3, respectively.

In order for an efficient separation factor in terms of the aerosols or particles, respectively, to be rendered harmless to be achieved, the nanofiber layer 3 should have a mean efficiency factor $E_m$ according to DIN EN 779 (July 1993) of at least 45%, in particular at least 55%, preferably at least 75%, particularly preferably at least 90%, most particularly preferably at least 95%. The nanofiber layer should furthermore have a mean separation factor $A_m$ according to DIN EN 779 (July 1993) of at least 55%, in particular at least 75%, preferably at least 90%, particularly preferably at least 95%, most particularly preferably at least 99%.

DIN EN 779 of July 1993 generally relates to the requirements, testing, and marking of particle air filters for the general room-air technology. According to this rule, the mean separation factor $A_m$ is determined by a gravimetric testing method, wherein repeated dusting of the specimen using a known quantity of the standardized artificial test dust in flowing air takes place up to a maximum final pressure loss of 250 Pa, wherein the separation factor is in each case determined from the mass ratios by weighing a suspended matter filter downstream of the specimen, wherein the mean separation factor $A_m$ applies as calculated from all individual measurements; in terms of further details in this regard, reference can be made to DIN EN 779. By contrast, the mean efficiency factor $E_m$ according to DIN 779 of July 1993 is measured by means of a coloration testing method by multiple measurements of the efficiency factor in relation to natural atmospheric dust in the air, wherein the specimen upon a first measurement in the new state is charged with a known quantity of standardized artificial testing dust according to DIN EN 779, and the determination of the efficiency factor is thereafter performed again until a final pressure loss of 450 Pa is achieved, wherein the measurement of the efficiency factor is based on the comparison of those testing air volumes which have in each case to be suctioned through a white suspended matter filter paper before and after the specimen, until said suspended matter filter papers are identically colored or discolored, respectively, wherein the mean efficiency factor $E_m$ applies as calculated from all individual measurements; in terms of further details in this regard, reference can be made to DIN EN 779.

Moreover, the nanofiber layer 3 for the purpose of achieving a good separation of particles and aerosols should have an integral initial transmittance $D_i$ according to DIN EN 1822 (April 1998; DEHS-Aerosol (Diethylhexylsebacat), Most Penetrating Particle Size=MPPS=0.1 to 0.3 µm) of at most 45%, in particular at most 40%, preferably at most 30%, particularly preferably at most 20%, most particularly preferably at most 10%.

The testing method according to DIN EN 1822 is carried out on unpolluted specimens using a liquid testing aerosol (DEHS=Diethylhexylsebacat), based on measured values for in each case a particle diameter corresponding to the transmittance maximum (so-called MPPS, here: 0.1 to 0.3 µm). In a first step of the examination, that particle size at which the maximum transmittance maximum (MPPS) is achieved is determined on the flat specimens of the filter medium, wherein the subsequent evaluation and classification of the filters takes place only for the MPPS. In a second step, the integral transmittance $D_i$, determined then by way of the exhaust face, for the MPPS and the pressure loss of the filter are measured, both at the nominal volumetric flow. In terms of further details in this regard, reference can be made to DIN EN 1822.

The nanofiber layer 3 should furthermore have a separation factor according to DIN EN 1822 (April 1998) of at least 45%, in particular at least 55%, preferably at least 75%, particularly preferably at least 90%, most particularly preferably at least 95%.

Moreover, the nanofiber layer 3 at an incident flow rate of 0.1 m/s in relation to particles and/or aerosols having diameters in the range from 0.1 to 0.3 µm should have a mean separation factor of at least 85%, in particular at least 90%, preferably at least 95%.

The nanofiber layer 3 at an incident flow rate of 0.1 m/s in relation to particles and/or aerosols having diameters ≥2 µm, in particular ≥1.5 µm, preferably ≥1.0 µm, should have in particular a mean separation factor of at least 97%, in particular at least 98%, preferably at least 99%.

According to one embodiment according to the invention it can moreover be provided that the nanofiber layer 3, in particular nanofibers 3' of the nanofiber layer 3, is/are present so as to partially invade the support material 2. In particular, the nanofiber layer 3 can extend in particular in part and/or in portions into the support material 2. This can be achieved, for example, in that the nanofiber layer 3 in the context of the production of the sheet filter material 1 according to the invention is applied to a not yet fully cured or dried, respectively, support material, or is pressed thereon, respectively. On account thereof, the bond between support material 2, on the one hand, and the nanofiber layer 3, on the other hand, can be further consolidated or stabilized, respectively.

In this context, the nanofiber layer 3, in particular the nanofibers 3' of the nanofiber 3, can extend into the support material 2 by way of at least 1%, in particular at least 5%, preferably at least 10%, of the thickness of the support material 2. In particular, the nanofiber layer 3, in particular the nanofibers 3' of the nanofiber layer 3, can extend into the support material 2 by way of at most 30%, in particular at most 25%, preferably at most 20%, of the thickness of the support material 2.

It can moreover be provided according to the invention that the sheet filter material 1 has at least one further nanofiber layer. In this context, the further nanofiber layer can be assigned to the foam-based or foam-shaped, respectively, support material 2. Moreover, the further nanofiber layer can be disposed on the side of the support material 2 that faces away from the nanofiber layer 3. In this context, the further nanofiber layer can in particular be fixed to or be brought to bond with, respectively, a (second) side 2b, in particular flat side, of the support material 2. In particular, the further nanofiber layer can comprise a multiplicity of nanofibers, or be composed thereof.

In principle, the further nanofiber layer can be constructed or configured, respectively, so as to be comparable or identical, respectively, to the nanofiber layer 3, such that reference to this end can be made to the above explanations pertaining to the nanofiber layer 3, said explanations likewise applying to the further nanofiber layer or to the nanofibers used to this end, respectively.

According to a preferred embodiment according to the invention it can moreover be provided that the sheet filter material 1, as illustrated in the figurative illustrations according to FIG. 2 and FIG. 3, furthermore (c) has at least one textile carrier 4. In this context, FIG. 2 and FIG. 3 highlight that the textile carrier 4 can have two opposite sides 4a, 4b, in particular flat sides.

Moreover, the textile carrier 4 can be assigned to the support material 2. In this context, the textile carrier 4 can be disposed on the side 2b of the support material 2 that faces away from the nanofiber layer 3, as is likewise schematically visualized in FIG. 2 and FIG. 3.

It can in particular be provided according to the invention that the textile carrier 4 is fixed to or brought to bond with, respectively, the support material 2.

As is illustrated in FIG. 2 and FIG. 3, it can be provided according to the invention in this context that the textile carrier 4 is fixed to or is brought to bond with, respectively, a (second) side 2b, in particular flat side, of the support material 2, in particular by way of a (first) side 4a, preferably a flat side, of the textile carrier 4.

On account of the use of a textile carrier 4, the sheet filter material 1 according to the invention can be further stabilized, and moreover be equipped in a targeted manner with special textile properties. Moreover, the textile carrier 4 in the context of the production of the sheet filter material 1 according to the invention can be used for receiving a foam structure, or a foam structure material, respectively, which is in particular not cured, or in particular not dried, and which is used for configuring the support material 2.

In general, the textile carrier 4 according to the invention, for example by means or as a result of, respectively, an inherent adhesiveness of the support material, can be fixed to or brought to bond with, respectively, the support material 2, in particular on the (second) side 2b of the support material 2, said inherent adhesiveness being present in particular in the production of the sheet filter material 1.

According to one alternative embodiment of the present invention, it can however also be provided that textile carrier 4, by means of using a bonding agent which is in particular applied in a discontinuous/punctiform manner, is fixed to and/or brought to bond with the support material 2, in particular on the (second) side 2b of the support material 2.

The textile carrier 4 can in particular be configured as a textile planar formation, preferably an air-permeable and/or water-vapor-permeable textile material, preferably a woven fabric, a warp-knitted or weft-knitted fabric, a circular-knitted or flat-knitted fabric, a cross-laid fabric, a non-woven, or a textile composite cloth.

Moreover, the textile carrier 4 can generally have an area weight in the range from 15 g/m² to 500 g/m², in particular in the range from 25 g/m² to 300 g/m², preferably in the range from 35 g/m² to 175 g/m².

According to the invention, it can in particular be provided that the textile carrier 4 is a textile planar formation composed of natural and/or synthetic fibers, preferably synthetic fibers (chemical fibers).

The textile carrier 4 can in particular be a textile planar formation with or from natural and/or synthetic fibers, in particular from the group of polyesters (PES), polyolefins such as polyethylene (PE) and polypropylene (PP), polyvinylchloride (CLF); polyvinylidene chloride (CLF); acetate (CA); triacetates (CTA); polyacryl (PAN), polyamide (PA); polyaramids; polyvinyl alcohol (PVAL); polyurethanes, polyvinyl esters; (methyl) acrylates; viscose (CV); lyocell; as well as the mixtures or combinations thereof.

The textile carrier 4 can have a thickness in the range from 0.005 to 10 mm, in particular in the range from 0.015 to 5 mm, preferably in the range from 0.02 to 1 mm. The term of the thickness of the textile carrier 4 herein is in particular understood to be the spacing of the (first) side 4a from the (second) side 4b of the textile carrier.

Moreover, the textile carrier 4 can have an air-permeability of at least 150 $l \cdot m^{-2} \cdot s^{-1}$, in particular at least 200 $l \cdot m^{-2} \cdot s^{-1}$, preferably at least 250 $l \cdot m^{-2} \cdot s^{-1}$, particularly preferably at least 400 $l \cdot m^{-2} \cdot s^{-1}$, most particularly preferably at least 800 $l \cdot m^{-2} \cdot s^{-1}$, at a flow resistance of 127 Pa.

As is illustrated in FIG. 3, it can moreover be provided according to the invention that the sheet filter material 1 furthermore (d) has at least one covering layer 5.

On account thereof, the nanofiber layer 3 can in particular be provided with an additional protection. Moreover, the sheet filter material 1 can be equipped with further textile properties, for example in terms of the visual appearance or the haptics thereof.

The covering layer 5 generally has two opposite sides 5a, 5b, in particular flat sides, as is likewise schematically illustrated in FIG. 3.

The covering layer 5 can be generally assigned to the nanofiber layer 3. In particular, the covering layer 5 can be assigned to the side 3b of the nanofiber layer 3 that faces away from the support material 2.

Moreover, the covering layer 5 can be disposed on the side 3b of the nanofiber layer 3 that faces away from the support material 2. To this end, reference can likewise be made to FIG. 3.

In this context, the covering layer 5 can be fixed to and/or be brought to bond with a (second) side 3b, in particular flat side, of the nanofiber layer 3, and specifically in particular by way of a (first) side 5a, preferably a flat side, of the covering layer 5, as is visualized in FIG. 3.

The covering layer 5 in the context of the present invention can be fixed to or be brought to bond with, respectively, the nanofiber layer 3 such that a permanent bond is also present in this regard.

In the context of the present invention it can be provided in this context that the covering layer 5 by means and/or as a result of an inherent adhesiveness of the nanofiber layer 3, in particular of the nanofibers 3' of the nanofiber layer 3, said inherent adhesiveness being in particular present in the production of the sheet filter material 1 and/or of the nanofiber layer 3 is fixed to or brought to bond with, respectively, the nanofiber layer 3, in particular on the (second) side 3b of the nanofiber layer 3.

However, it is also possible according to the invention that the covering layer 5 by means of using a bonding agent which is applied in particular in a discontinuous/punctiform manner is fixed to and/or brought to bond with the nanofiber layer 3, in particular on the (second) side 3b of the nanofiber layer 3.

The covering layer 5 can generally be configured as a textile planar formation, preferably an air-permeable and/or water-vapor-permeable textile material, preferably a woven fabric, a warp-knitted or weft-knitted fabric, a circular-knitted or flat-knitted fabric, a cross-laid fabric, a nonwoven, or a textile composite cloth.

In this context, the covering layer 5 can have an area weight in the range from 5 g/m² to 400 g/m², in particular in the range from 10 g/m² to 200 g/m², preferably in the range from 20 g/m² to 150 g/m².

It can be provided according to the invention that the covering layer 5 is a textile planar formation composed of natural and/or synthetic fibers, preferably synthetic fibers (chemical fibers).

In particular, the covering layer 5 can be a textile planar formation with or from natural and/or synthetic fibers, in particular from the group of polyesters (PES), polyolefins such as polyethylene (PE) and polypropylene (PP), polyvinylchloride (CLF); polyvinylidene chloride (CLF); acetate (CA); triacetates (CTA); polyacryl (PAN), polyamide (PA); polyaramids; polyvinyl alcohol (PVAL); polyurethanes, polyvinyl esters; (methyl) acrylates; viscose (CV); lyocell; as well as the mixtures or combinations thereof.

Moreover, the covering layer 5 can have a thickness in the range from 0.001 to 8 mm, in particular in the range from 0.005 to 4 mm, preferably in the range from 0.01 to 0.9 mm.

The thickness of the covering layer 5b is generally understood to be in particular the spacing of the (first) side Sa from the (second) side 5b of the covering layer 5.

Moreover, the covering layer 5 can have an air permeability of at least 200 $l \cdot m^{-2} \cdot s^{-1}$, in particular at least 250 $l \cdot m^{-2} \cdot s^{-1}$, preferably at least 300 $l \cdot m^{-2} \cdot s^{-1}$, particularly preferably at least 450 $l \cdot m^{-2} \cdot s^{-1}$, most particularly preferably at least 850 $l \cdot m^{-2} \cdot s^{-1}$, at a flow resistance of 127 Pa.

According to one further embodiment according to the invention, it can moreover be provided that the sheet filter material 1 furthermore has at least one adsorption layer 6, as is illustrated in FIG. 4. On account of the sheet filter material 1 according to the invention being equipped with at least one adsorption layer 6, the protective function of the sheet filter material 1 in relation to chemical, biological or radioactive, respectively, harmful and toxic substances can be further increased, since the sheet filter material 1 according to the invention based on the adsorption layer 6 is additionally equipped with adsorptive properties.

According to the invention it is preferable herein that the adsorption layer 6 comprises a multiplicity of individual or discrete, respectively, adsorber particles 6', or is formed therefrom, as is likewise schematically illustrated in FIG. 4.

FIG. 4 highlights moreover that the adsorption layer 6 can have two opposite sides 6a, 6b, in particular flat sides.

In general, it is provided according to the invention that the adsorption layer 6 is assigned to the support material 2. In this context, it is preferable according to the invention that the adsorption layer 6 is disposed on the (second) side 2b of the support material 2 that faces away from the nanofiber layer 3, as is likewise visualized in FIG. 4.

The adsorption layer 6 in the context of the present invention should generally be configured so as to be discontinuous. It can in particular be provided according to the invention that the adsorption layer 6 is configured as an adsorption sheet filter. On account thereof, it is guaranteed, on the one hand, that the sheet filter material 1 according to the invention overall has a high air-permeability or water-vapor-permeability, respectively, and that the adsorptive properties and thus the overall protective function of the sheet filter material 1 according to the invention are yet again improved by virtue of the ready accessibility of the adsorption layer 6, or of the adsorber particles 6', on the other hand.

It is in particular the case in the context of the present invention such that the nanofiber layer 3, the foam-based or foam-shaped, respectively, support material 2, as well as the optionally present adsorption layer 6 in terms of providing the protective function in question are mutually complementary in functional terms, beyond the pure sum of the protective effects of the individual layers. In particular, the adsorption layer 6, in terms of harmful or toxic substances to be adsorbed, is relieved by the nanofiber layer 3 or the support material 2, respectively, since an effective aerosol or particle filter function, respectively, is already provided by said layers and a majority of the harmful or toxic substances, respectively, are thus trapped before reaching the adsorption layer 6. With a view to the use or processing, respectively, of the sheet filter material 1 according to the invention for or to, respectively, protective equipment, in particular protective clothing, it is in particular provided herein that the adsorption layer 6 in the worn state or use state, respectively, is disposed on the side of the sheet filter material 1 or of the support material 2, respectively, that is assigned to the user or the wearer, respectively, of the clothing, on the one hand, or that the nanofiber layer 3 is disposed on the side of the sheet filter material 1 or of the support material 2, respectively, that faces away from the user or the wearer, respectively, of the clothing, on the other hand.

According to a first embodiment according to the invention, it can be provided that the adsorption layer 6 is fixed to or brought to bond with, respectively, the support material 2.

According to the invention it can in particular be provided herein that the adsorption layer 6 is fixed to or brought to bond with, respectively, a (second) side 2b, in particular flat side, of the support material 2. In this regard, the fixing or the bringing to bond, respectively, can take place in particular by way of a (first) side 6a, preferably a flat side, of the adsorption layer 6, as is schematically visualized in FIG. 4.

In the context of this embodiment according to the invention it can be provided herein that the adsorption layer 6, in particular the adsorber particles 6' of the adsorption layer 6, by means of using a bonding agent which is in particular applied in a discontinuous/punctiform manner, is/are fixed to and/or brought to bond with the support material 2, in particular on the (second) side 2b of the support material 2. An adhesive mesh or the like can also be used for fixing in this regard, for example.

According to the invention it can moreover be provided that the adsorption layer 6, in particular the adsorber particles 6' of the adsorption layer 6, is/are fixed to or brought to bond with, respectively, on the likewise provided textile carrier 4.

In this regard, the adsorption layer 6, in particular the adsorber particles 6' of the adsorption layer 6, can be fixed to or be brought to bond with, respectively, a (first) side 4a, in particular flat side, of the textile carrier 4, in particular by way of a (second) side 6b, preferably a flat side, of the adsorption layer 6. A bonding agent which is in particular applied in a discontinuous/punctiform manner can also be used in this regard.

It can in particular be provided according to the invention that the adsorption layer 6, in particular the adsorber particles 6' of the adsorption layer 6, is/are disposed between the support material 2 and the textile carrier 4. In this context, the adsorption layer can be fixed to or be brought to bond with, respectively, a (second) side 2b, in particular a flat side, of the support material 2, in particular by way of a (first) side 6a, preferably a flat side, of the adsorption layer 6. In this context, it can be likewise provided that the adsorption layer 6, in particular the adsorber particles 6' of the adsorption layer 6, is/are fixed to or brought to bond with, respectively, a (first) side 4a, in particular a flat side, of the textile carrier 4, in particular by way of a (second) side 6b, preferably a flat side, of the adsorption layer 6. A bonding agent which is in particular applied in a discontinuous/punctiform manner can likewise be used for the respective fixing in each case. An adhesive mesh or the like can also be used for the respective fixing, for example.

An overall stable bond in terms of the sheet filter material 1 according to the invention is provided in this way.

According to the invention, it is in principle also possible that the adsorption layer 6, in particular the adsorber particles 6' of the adsorption layer 6, is/are fixed to or brought to bond with, respectively, a (second) side 4b of the textile carrier 4, in particular by way of a (first) side 6a, in particular flat side, of the adsorption layer 6. In this case, it applies in particular such that the textile carrier 4 is disposed between the support material 2, on the one hand, and the adsorption layer 6, on the other hand.

According to an embodiment which is particularly preferred according to the invention, it is in particular provided that the adsorption layer 6, in particular the adsorber particles 6' of the adsorption layer 6, is/are not assigned to the nanofiber layer 3, or that the adsorption layer 6, in particular the adsorber particles 6' of the adsorption layer 6, is/are not disposed between the support material 2 and the nanofiber layer 3. As has been set forth above, it is specifically in particular the case according to the invention such that the nanofiber layer 3 is assigned to the foam-based or foam-shaped, respectively, support material 2, or is fixed thereto and/or brought to bond therewith, respectively, without any further intervening layers. The configuration of a particularly stable bond, on the one hand, and an optimal interaction or reinforcing effect, respectively, of the respective layers 2, 3, 6 in terms of the connection of the protective function provided overall is guaranteed in this way, on the other hand.

However, according to a less preferred embodiment it can also be provided in principle that the adsorption layer 6, in particular the adsorber particles 6' of the adsorption layer 6, is/are fixed to or are brought to bond with, respectively, the nanofiber layer 3, and specifically in particular on the second side 3b of the nanofiber layer 3, or in particular on the side 3b of the nanofiber layer 3 that faces away from the support material 2, preferably by means of a bonding agent which is in particular applied in a discontinuous/punctiform manner, or by means of an adhesive mesh or the like, respectively.

According to a further embodiment according to the invention, it is in particular the case such that the adsorption layer 6, in particular the adsorber particles 6' of the adsorption layer 6, is/are not fixed to the support material 2, or not to the textile carrier 4, or in that the adsorption layer 6 is not brought to bond with the support material 2, or not with the textile carrier 4, respectively. In an analogous manner, it is in particular provided according to the invention that the adsorption layer 6, in particular the adsorber particles 6' of the adsorption layer 6, is/are not fixed to or brought to bond with, respectively, the nanofiber layer 3.

In this context, it can in particular be the case according to the invention such that the adsorption layer 6 is configured as a separate layer, or as a layer which is not connected to the support material 2, or not to the nanofiber layer 3, or not to the textile carrier 4, respectively, or is not configured so as to be fixed to or brought to bond with the aforementioned layers 2, 3, 4. The adsorption layer 6 can thus represent, so to speak, an unconnected or independent, respectively, layer within the sheet filter material 2 according to the invention. The flexibility or flexural capability, respectively, of the sheet filter material according to the invention can be increased on account thereof, for example. Moreover, an enhanced adaptability of the sheet filter material 1 according to the invention, in particular in terms of the respective specific application or use, respectively, of the material results on account thereof.

Insofar as the present embodiment of the present invention is concerned, according to which the adsorption layer 6 is not fixed to or is not brought to bond with, respectively, the further layers 2, 3, 4, it is thus advantageous in the context of the present invention when the adsorption layer 6 is fixed to or brought to bond with, respectively, a separate, in particular, textile carrier. In this regard, the adsorption layer 6 and the separate, in particular textile, carrier can configure a separate or independent composite, or a composite which is not fixed to any of the further layers 2, 3, 4 of the sheet filter material 1, or not brought to bond with, any of the further layers 2, 3, 4 of the sheet filter material 1, respectively. The stability of the adsorption layer 6 can be increased as a result of the use of a (further) textile carrier for said adsorption layer 6.

In the context of the present invention, a multiplicity of different adsorption materials can be used for the adsorber particles 6' in order for the adsorption layer 6 to be configured:

The adsorber particles 6' of the adsorption layer 6 can in particular be selected from the group of (i) in particular particulate activated carbon and/or activated carbon particles, preferably in the form of activated carbon particles in the form of granules ("granular carbon") or in the form of spheres ("spherical carbon");

(ii) zeolites, in particular natural and/or synthetic zeolites;

(iii) molecular screens, in particular zeolitic molecular screens, synthetic molecular screens, and/or in particular synthetic molecular screens based on carbon, oxides and/or glass;

(iv) metal oxide particles and/or metal particles;

(v) ion-exchange resins, in particular polydisperse and/or monodisperse cation exchangers and/or anion exchangers, in particular of the gel type and/or the macroporous type;

(vi) inorganic oxides, in particular silicon dioxides, silica gels, and/or aluminum oxides;

(vii) porous organic polymers and/or porous organic/inorganic hybrid polymers and/or organometallic framework materials, in particular MOFs (Metal Organic Framework), COFs (Covalent Organic Framework), ZIFs (Zeolite Imidazolate Framework), POMs (Polymer Organic Material) and/or OFCs;

(viii) mineral granules;

(ix) clathrates; as well as (x) the mixtures and/or combinations thereof.

According to an embodiment which is particularly preferred according to the invention, the adsorber particles 6' of the adsorption layer 6 can be formed from or composed of activated carbon, in particular particulate activated carbon and/or activated carbon particles, preferably in the form of activated carbon particles in form of granules ("granular carbon") or in the form of spheres ("spherical carbon").

The respective particle-forming materials of the adsorber particles 6' used according to the invention are generally known per se to the person skilled in the art, and the person skilled in the art is always capable of selecting and tuning the respective particle-forming materials with a view to equipping the sheet filter material according to the invention with special properties, in particular adsorption properties, in light of the present invention.

In terms of the adsorber particles 6 which can be used according to the invention, reference can also be made to the explanation hereunder. Moreover, in terms of further details pertaining to the MOF materials which can likewise be used according to the invention, reference can in particular be made to the international patent application WO 2009/096184 A1 as well as to the parallel German patent application DE 10 2008 005 218 A1, the respective disclosure thereof in this regard herewith being fully incorporated by reference.

In as far as the diameter, or the mean diameter $D_{50}$, of the adsorber particles 6' is concerned, said diameter can thus vary within wide ranges. However, particularly positive results are obtained when the diameter of the adsorber particles 6', in particular of the particulate activated carbon and/or of the activated carbon particles, is in the range from 0.005 mm to 5 mm, preferably in the range from 0.01 mm to 2.5 mm, preferably in the range from 0.015 mm to 1 mm, particularly preferably in the range from 0.02 mm to 0.8 mm, most particular preferably in the range from 0.03 mm to 0.6 mm.

Moreover, the mean diameter $D_{50}$ of the adsorber particles 6', in particular of the particulate activated carbon and/or of the activated carbon particles, can be in the range from 0.01 mm to 4 mm, in particular in the range from 0.02 mm to 2 mm, preferably in the range from 0.03 mm to 0.75 mm, particular preferably in the range from 0.04 mm to 0.6 mm, most particularly preferably in the range from 0.05 mm to 0.55 mm.

The respective particle sizes can be determined in particular based on the method according to ASTM D2862-97/04. Moreover, the aforementioned sizes can be determined by way of determination methods based on a screen analysis, based on x-ray diffraction, laser diffraction, or the like. The respective determination methods are well known per se to the person skilled in the art such that no further explanations are required in this regard.

In general, the adsorber particles 6', in particular the particulate activated carbon and/or the activated carbon particles, can be used or be present, respectively, in a quantity in the range from 5 g/m$^2$ to 500 g/m$^2$, in particular in the range from 10 g/m$^2$ to 400 g/m$^2$ preferably in the range from 15 g/m$^2$ to 300 g/m$^2$, preferably in the range from 20 g/m$^2$ to 250 g/m$^2$, particularly preferably in the range from 30 g/m$^2$ to 225 g/m$^2$, most particularly preferably in the range from 40 g/m$^2$ to 200 g/m$^2$, furthermore preferably in the range from 60 g/m$^2$ to 200 g/m$^2$.

In particular, the sheet filter material 1, in particular the adsorption layer 6, can comprise the adsorber particles 6', in particular the particulate activated carbon and/or the activated carbon particles, in a quantity in the range from 5 g/m$^2$ to 500 g/m$^2$, in particular in the range from 10 g/m$^2$ to 400 g/m$^2$, preferably in the range from 15 g/m$^2$ to 300 g/m$^2$, preferably in the range from 20 g/m$^2$ to 250 g/m$^2$, particularly preferably in the range from 30 g/m$^2$ to 225 g/m$^2$, most particularly preferably in the range from 40 g/m$^2$ to 200 g/m$^2$, furthermore preferably in the range from 60 g/m$^2$ to 200 g/m$^2$. According to the invention, in particular by virtue of the aerosol or particle filter function provided by the nanofiber layer 3, correspondingly minor quantities in the application of the adsorber particles 6' can be implemented, this leading to a further reduction of the overall area weight of the sheet filter material 1 according to the invention.

In as far as the activated carbon, or the particulate activated carbon or activated carbon particles, respectively, (hereunder also referred to only as activated carbon) used or applied, respectively, in the context of the present invention is concerned per se, the presently listed parameter indications in terms of the underlying activated carbon or particulate activated carbon or active carbon particles, respectively, are thus determined using standardized or explicitly indicated determination methods, or using determination methods which are familiar to the person skilled in the art per se. In particular the parameter indications relating to the characterization of the porosity of the pore size distribution and other adsorption properties, in each case derive generally from the corresponding oxygen absorption isotherm of the respective activated carbon or of the measured product, respectively. Moreover, the pore distribution, in particular also in terms of the content of micropores in relation to the overall pore volume, can be determined based on DIN 66135-1.

According to an embodiment preferred according to the invention, according to which activated carbon or activated carbon particles, respectively, is/are used as adsorber particles 6' or as adsorption material, respectively, the activated carbon can be obtainable by carbonizing and subsequently activating a synthetic and/or not natural initial material, in particular based on organic polymers.

In this context, the activated carbon can be obtained from an initial material based on organic polymers, in particular based on sulfonated organic polymers, preferably based on divinyl-benzene cross-linked polystyrene, preferably based on styrene/divinyl-benzene copolymers, in particular by carbonizing and subsequently activating the initial material. In this context, the content of divinyl benzene in the initial material can be in the range from 1% by weight to 20% by weight, in particular in the range from 1% by weight to 15% by weight, preferably in the range from 1.5% by weight to 12.5% by weight, preferably in the range from 2% by weight to 10% by weight.

According to the invention, the initial material for the activated carbon can in particular be a sulfonated ion-exchange resin and/or an ion-exchange resin containing sulfonic acid groups, in particular of the gel type.

According to an embodiment which is particularly preferred according to the invention, a polymer-based spherical activated carbon (PBSAC) can be used as activated carbon.

The activated carbon can in particular be a polymer-based spherical activated carbon (PBSAC). Activated carbons of this type are distinguished by outstanding adsorption properties in relation to the aforementioned harmful or toxic substances, and by outstanding mechanical properties such as a high material hardness as well as a high hardness in terms of abrasion.

The activated carbon used herein can in principle be obtained according to known methods of the prior art. For this purpose, in particular spherical sulfonated organic polymers, in particular based on divinyl-benzene-cross-linked polystyrene, are carbonized and subsequently activated so as to form the respective activated carbon, in particular as has been stated previously. For further details in this regard, reference can be made, for example, to publications DE 43 28 219 A1, DE 43 04 026 A1, DE 196 00 237 A1, as well as EP 1 918 022 A1, or to parallel U.S. Pat. No. 7,737,038 B2 which is part of the same pattern family, the respective content of said publication is herewith being fully incorporated by reference.

Activated carbons or activated carbon particles, respectively, used in the context of the present invention are generally commercially available or obtainable, respectively. In particular, activated carbons which are produced or marketed, respectively, by Blücher GmbH, Erkrath, Germany, can be used, for example.

It has proven advantageous in the context of the present invention when the activated carbon used according to the invention has a furthermore specified overall pore volume, in particular an overall pore volume according to Gurvich.

In this context, the activated carbon can have an overall pore volume, in particular an overall pore volume according to Gurvich, in the range from 0.4 cm$^3$/g to 3.9 cm$^3$/g, in particular in the range from 0.45 cm$^3$/g to 3.5 cm$^3$/g, preferably in the range from 0.5 cm$^3$/g to 3 cm$^3$/g, particularly preferably in the range from 0.6 cm$^3$/g to 2.5 cm$^3$/g, most particularly preferably in the range from 0.5 cm$^3$/g to 1.5 cm$^3$/g.

In particular, at least 65%, in particular at least 70%, preferably at least 75%, preferably at least 80%, of the overall pore volume, in particular of the overall pore volume according to Gurvich, of the activated carbon can be formed by pores having pore diameters of at most 50 nm, in particular by micropores and/or mesopores.

In particular, 50% to 95%, in particular 60% to 90%, preferably 70% to 85%, of the overall pore volume, in particular of the overall pore volume according to Gurvich, of the activated carbon can be formed by pores having pore diameters of at most 50 nm, in particular by micropores and/or mesopores.

Moreover, 1% to 60%, in particular 5% to 50%, preferably 10% to 40%, preferably 15% to 35%, of the overall pore volume, in particular of the overall pore volume according to Gurvich, of the activated carbon can be formed by pores having pore diameters of more than 2 nm, in particular by mesopores and/or macropores.

In particular, the activated carbon can have a pore volume formed by pores having pore diameters of at most 2 nm (i.e. 2 nm), in particular a micropore volume according to Carbon Black, in the range from 0.05 cm$^3$/g to 2.5 cm$^3$/g, in particular in the range from 0.15 cm$^3$/g to 2 cm$^3$/g, preferably in the range from 0.3 cm$^3$/g to 1.5 cm$^3$/g.

In particular, 15% to 98%, in particular 25% to 95%, preferably 35% to 90%, of the overall pore volume of the activated carbon can be formed by pores having pore diameters of at most 2 nm, in particular by micropores.

In terms of the microporous activated carbon which can be used according to the invention, reference can moreover be made going back to the European patent application EP 1 918 022 A1 by the applicant per say, as well as to parallel US 2008/0107589 A1, the respective disclosure thereof herewith being fully incorporated by reference.

In as far as the determination of the overall pore volume according to Gurvich is concerned, this is a measurement/determination method which is well known per se to the person skilled in this art in this field. In terms of further details with regard to the determination of the overall pore volume according to Gurvich, reference can be made, for example, to L. Gurvich (1915), *J. Phys. Chem. Soc. Russ.* 47, 805, as well as to S. Lowell et al., Characterization of Porous Solids and Powders: Surface Area Pore *Size and Density, Kluwer Academic Publishers, Article Technology Series*, pages 111 ff. The pore volume of the activated carbon can in particular be determined based on the Gurvich rule according to the formula $V_P = W_a / \rho_l$, where $W_a$ is the adsorbed quantity of an underlying adsorbant and pi is the thickness of the adsorbent used (cf. also formula (8.20) according to page 111, chapter 8.4.) of S. Lowell et al.).

The determination method according to Carbon Black is known per se to the person skilled in the art, wherein in terms of further details pertaining to the determination of the pore surface and of the pore volume according to Carbon Black reference can be made, for example to R. W. Magee, *Evaluation of the External Surface Area of Carbon Black by Nitrogen Adsorption, Presented at the Meeting of the Rubber Division of the American Chem. Soc.*, October 1994, e.g. referred to in: *Quantachrome Instruments, AUTOSORB-1, AS1 Win Version 1.50, Operating Manual, OM, 05061, Quantachrome Instruments* 2004, Florida, USA, pages 71 ff. The respective evaluation can in particular take place by means of the t-plot method.

In terms of further details pertaining to the determination of the BET surface, or to the BET method, respectively, reference can be made to aforementioned ASTM D6556-04 as well as to Römpp Chemielexikon, 10$^{th}$ edition, Georg Thieme Publishers, Stuttgart/New York, keyword: "BET-Methode" ("BET method"), including the literature cited therein, and to Winnacker-Küchler (3$^{rd}$ edition), volume 7, pages 93 ff. as well as to Z. Anal. Chem. 238, pages 187 to 193 (1968).

In the context of the present invention, the term "micropores" refers to pores of this type having pore diameters of less than 2 nm, whereas the term "mesopores" refers to pores having pore diameters in the range from 2 nm (i.e. 2 nm inclusive) to 50 nm inclusive, and the term "macropores" refers to pores of this type having pore diameters of more than 50 nm (i.e. >50 nm).

Furthermore, the activated carbon can have a specific BET surface in the range from 600 m$^2$/g to 4,500 m$^2$/g, in particular in the range from 800 m$^2$/g to 3,500 m$^2$/g, preferably in the range from 1,000 m$^2$/g to 3,000 m$^2$/g, particularly preferably in the range from 1,200 m$^2$/g to 2,750 m$^2$/g, most particularly preferably in the range from 1,300 m$^2$/g to 2,500 m$^2$/g.

The determination of the specific surface according to BET is in principle known per se to the person skilled in the art so that no further details need to be explained in this regard. All of the BET surface indications refer to the determination according to ASTM D6556-04. In the context of the present invention, the so-called MultiPoint BET determination method (MP BET) in a partial pressure range $p/p_0$ from 0.05 to 0.1 is applied generally and to the extent not stated otherwise.

In particular, the activated carbon can have a surface formed by pores having pore diameters of at most 2 nm, in particular by micropores, in the range from 400 to 3,500 m$^2$/g, in particular in the range from 500 to 3,000 m$^2$/g, preferably in the range from 600 to 2,500 m$^2$/g, preferably in the range from 700 to 2,000 m$^2$/g.

In general, the activated carbon can have a surface formed by pores having pore diameters in the range from 2 nm to 50 nm, in particular by mesopores, in the range from 200 to 2,000 m$^2$/g, in particular in the range from 300 to 1,900 m$^2$/g, preferably in the range from 400 to 1,800 m$^2$/g, preferably in the range from 500 to 1,700 m$^2$/g. The activated carbon which can be used according to the invention can moreover have a mean pore diameter in the range from 0.1 nm to 55 nm, in particular in the range from 0.2 nm to 50 nm, preferably in the range from 0.5 nm to 45 nm, preferably in the range from 1 nm to 40 nm.

The sheet filter material 1 according to the invention overall has outstanding properties, as set forth hereunder.

The sheet filter material 1 according to the invention can thus be self-supporting. The sheet filter material 1 can generally be configured as a composite material. The sheet filter material 1 according to the invention herein has in particular a high mechanical stability and simultaneously a high flexural capability of the overall material.

In particular, the sheet filter material 1 according to the invention can have an overall area weight in the range from 10 g/m² to 800 g/m², in particular in the range from 20 g/m² to 600 g/m², preferably in the range from 50 g/m² to 400 g/m², preferably in the range from 75 g/m² to 300 g/m², particularly preferably in the range from 100 g/m² to 200 g/m².

Moreover, the sheet filter material 1 can have an air permeability of at least 10 l·m⁻²·s⁻¹, in particular at least 25 l·m⁻²·s⁻¹, preferably at least 30 l·m⁻²·s⁻¹, preferably at least 40 l·m⁻²·s⁻¹, particularly preferably at least 50 l·m⁻²·s⁻¹, most particularly preferably at least 100 l·m⁻²·s⁻¹, at a flow resistance of 127 Pa.

As has been set forth above, the sheet filter material 1 can be configured so as to be water-proof and/or water-repellent. The sheet filter material 1 can in particular have a water column of at least 500 mm, in particular at least 600 mm, preferably at least 700 mm, measured according to DIN EN 20 811:1992 (August 1992). It can moreover be provided according to the invention that the sheet filter material 1 has a water column in the range from 500 mm to 2,500 mm, in particular in the range from 600 mm to 2,000 mm, preferably in the range from 700 mm to 1,500 mm, measured according to DIN EN 811:1992 (August 1992).

Moreover, the sheet filter material 1 at 25° C. can have a water-vapor permeability of at least 10 l/m² per 24 h, in particular at least 20 l/m² per 24 h, preferably at least 30 l/m² per 24 h.

In this context, the sheet filter material 1 can have a water-vapor transmittance resistance $R_{et}$ at stationary conditions, measured according to DIN EN 31 092:1993 (February 1994) and international standard ISO 11 092, at 35° C., of at most 25 (m²·Pascal)/Watt, in particular at most 20 (m²·Pascal)/Watt, preferably at most 10 (m²·Pascal)/Watt.

Furthermore, the sheet filter material 1 can have an overall thickness in the range from 0.1 mm to 30 mm, in particular in the range from 0.2 mm to 20 mm, preferably in the range from 0.5 mm to 10 mm, preferably in the range from 0.6 mm to 6 mm, particularly preferably in the range from 0.8 mm to 2 mm.

Moreover, the sheet filter material 1 can have a mean efficiency factor $E_m$ according to DIN EN 779 (July 1993) of at least 50%, in particular at least 60%, preferably at least 80%, particularly preferably at least 95%, most particularly preferably at least 97%.

Moreover, the sheet filter material 1 can have a mean separation factor $A_m$ according to DIN EN 779 (July 1993) of at least 60%, in particular at least 80%, preferably at least 95%, particularly preferably at least 99%, most particularly preferably at least 99.5%.

Moreover, the sheet filter material 1 can have a separation factor performance according to DIN EN 1822 (April 1998) of at least 50%, in particular at least 60%, preferably at least 80%, particularly preferably at least 95%, most particularly preferably at least 97%.

Furthermore, the sheet filter material 1 according to the invention can also have an outstanding protective function in relation to harmful or toxic substances, in particular chemical warfare agents. The sheet filter material 1 according to the invention can thus have a barrier effect in relation to harmful and/or toxic substances, in particular chemical warfare agents, in particular Bis[2-chloroethyl] sulfide, determined according to method 2.2 of CRDC-SP-84010, of at most 4.2 µg/cm² per 24 h, in particular at most 4 µg/cm² per 24 h, preferably at most 3.5 µg/cm² per 24 h, preferably at most 3 µg/cm² per 24 h, particularly preferably at most 2.5 µg/cm² per 24 h, most particularly preferably at most 2 µg/cm² pro 24 h.

The present invention also relates to the aspect according to the invention, according to which the textile sheet filter material 1 according to the invention is obtainable by the method for the production thereof described hereunder. The present invention thus also relates to a textile sheet filter material 1, in particular having an aerosol and/or particle filter function, preferably having a protective function in relation to chemical, biological and/or chemical harmful and toxic substances, wherein the sheet filter material 1 is obtainable by the method according to the invention described hereunder.

A further subject matter of the present invention, according to a further aspect of the present invention, is moreover a method for producing a sheet filter material in particular as has been described above, in particular having an aerosol and/or particle filter function, preferably having a protective function in relation to chemical, biological and/or radioactive harmful and toxic substances, wherein the method comprises the following steps:

a) providing an air-permeable and/or water-vapor-permeable, preferably planar, foam-based and/or foam-shaped support material having to opposite sides, in particular flat sides;

b) applying an air-permeable and/or water-vapor-permeable, preferably planar, nanofiber layer, in particular an aerosol and/or particle filter nanofiber layer, wherein the nanofiber layer comprises a multiplicity of nanofibers or is composed thereof, to the foam-based and/or foam-shaped support material, in particular on a (first) side, in particular a flat side, of the foam-based and/or foam-shaped support material in such a manner that the nanofiber layer is fixed to and/or is brought to bond with the support material, in particular on the (first) side, in particular a flat side, of the support material.

According to one embodiment preferred according to the invention, it can be provided in the context of the method according to the invention that the sheet filter material is equipped or provided, respectively, (c) with a textile carrier. An additional layer (c) in the form of a textile carrier can thus be provided. In this context, the textile carrier can be assigned to the support material. The textile carrier can in particular be disposed on the (second) side of the support material that faces away from the nanofiber layer.

In the context of the production of the protective material according to the invention, one can herein generally proceed in such a manner that an initially intact, not dried or not (fully) cured, respectively, foam for providing the foam-based or foam-shaped, respectively, support material is applied to a textile carrier, or to the removable carrier layer or the like, respectively, wherein the drying conditions (temperature or the like) can be chosen in such a manner, for example, that a destruction or opening, respectively, of the underlying pore structure takes place in the context of the drying. In this context, an introduction of mechanical energy into the foam system can also take place for example or be carried out, respectively. In the context of the curing or drying, respectively, a break-up or break-down or destruction, or a disintegration or opening, respectively, of the foam system so as to obtain the broken or open-pored, respectively, foam or polymer foam, respectively, or the corresponding foam-based or foam-shaped, respectively, support material in the dried or cured, respectively, state can thus take place, wherein the layered, contiguous construction of the support material per se is fundamentally preserved. Subsequently, the nanofiber layer, or the nanofibers underlying the nanofiber layer, respectively, can be applied to the thus obtained foam-based or foam-shaped, respectively, support material, for example by means of electrospinning or the like. The concept according to the invention herein also enables the support material herein to also be equipped in a homogenous or uniform manner, respectively, with the nanofibers or with the nanofiber layer, respectively wherein low area weights of the support material or of the nanofiber layer, respectively, can also be implemented in this context.

According to a first embodiment according to the invention, one can proceed as follows in order for the filter material according to the invention to be produced:

According to this embodiment, the providing or producing, respectively, of the support material can take place by applying, in particular fixing or bringing to bond, respectively, the support material on a textile carrier.

In this context, the support material can be applied to the textile carrier in particular in the form of a foamed, preferably foamed under the introduction of mechanical energy, aqueous or organic, preferably aqueous, solution or dispersion, respectively, of a foam structure material (foam structure polymer).

In particular, drying or curing, respectively, in particular cross-linking, of the support material in the form of the foamed solution or dispersion, respectively, of the foam structure material can be subsequently carried out, in particular in association with an open-pored configuration of the foam provided by the foamed solution and/or dispersion of the foam structure material, or in particular in association with breaking the foam provided by the foamed solution and/or dispersion of the foam structure material, respectively, in particular such that the support material is obtained as a dried or cured, respectively, in particular cross-linked, open-pored or broken, respectively, foam of the foam structure material.

In this way, the support material can in particular be fixed to and/or be brought to bond with the textile carrier.

According to a second embodiment according to the invention, one can alternatively also proceed as follows:

The providing or producing, respectively, of the support material can thus take place by applying the support material to a removable, in particular strippable, carrier layer, preferably to a carrier paper.

In this context, the support material can be applied to the removable carrier layer in the form of a foamed, preferably foamed under the introduction of mechanical energy, aqueous or organic, preferably aqueous, solution or dispersion, respectively, of a foam structure material (foam structure polymer).

Drying or curing, respectively, in particular cross-linking, of the support material in the form of the foamed solution or dispersion, respectively, of the foam structure material can subsequently be carried out, in particular in association with an open-pored configuration of the foam provided by the foamed solution or dispersion, respectively, of the foam structure material, or in particular in association with breaking the foam provided by the foamed solution or dispersion, respectively, of the foam structure material, respectively, in particular such that the support material is obtained as a dried or cured, respectively, in particular cross-linked, open-pored or broken, respectively, foam, or broken foam structure of the foam structure material, respectively.

The thus obtained support material, in particular in the form of the dried or cured, respectively, in particular cross-linked, open-pored or broken, respectively, foam of the foam structure material, can subsequently be released, in particular stripped, from the removable carrier layer.

In this context, the thus obtained support material can subsequently be applied to a textile carrier, in particular fixed thereto or brought to bond therewith, respectively, in particular by means of a bonding agent which is preferably applied in a discontinuous/punctiform manner.

According to this embodiment according to the invention, the nanofiber layer can be applied to the support material before or after removing or releasing, respectively, the removable carrier layer, in particular as presently described.

Insofar as the aforementioned embodiments of the method according to the invention are concerned overall, the foaming of the foamed solution or dispersion, respectively, of the foam structure material can thus take place by the introduction of gas or air, respectively, into the solution or dispersion, respectively, of the foam structure material. The introduction of gas or air, respectively, herein can be performed by injecting, stirring, vibrating, agitating, blowing gas and/or air, and/or by introducing gas and/or air into the solution and/or dispersion of the foam structure material by shear force. In this context, the foamed solution and/or dispersion of the foam structure material can be set to a foam liter weight in the range from 50 g/l to 500 g/l, in particular in the range from 75 g/l to 400 g/l, preferably in the range from 100 g/l to 300 g/l.

In general, the applying of the support material to the textile carrier, or to the removable carrier layer, respectively, can be carried out by rolling and/or squeegeeing. In particular the rolling and/or the squeegeeing is carried out by means of knife-over-roll squeegeeing, knife-on-air squeegeeing, stencil application and/or an application using the direct-roll-on-roll method. Moreover the rolling and/or the squeegeeing can be carried out by means of an open squeegee system and/or closed squeegee system.

In general, the support material in the form of the foamed solution and/or dispersion of the foam structure material can be applied to the textile carrier or to the removable carrier layer at a quantity in the range from 10 $g/m^2$ to 150 $g/m^2$, in particular in the range from 20 $g/m^2$ to 100 $g/m^2$, preferably in the range from 40 $g/m^2$ to 80 $g/m^2$.

Moreover, the support material in the form of the foamed solution or dispersion, respectively, of the foam structure material can be applied to the textile carrier to the removable carrier layer at a thickness in the range from 0.01 mm to 2 mm, in particular in the range from 0.05 mm to 1.5 mm, preferably in the range from 0.1 mm to 0.75 mm, preferably in the range from 0.15 mm to 0.5 mm.

Moreover, the drying or curing, respectively, of the support material can be carried out at a temperature in the range from 30° C. to 250° C., in particular 50° C. to 200° C., preferably 70° C. to 180° C., preferably 90° C. to 160° C.

Moreover, the drying and/or curing can be carried out for a temporal duration in the range from 0.1 min to 15 min, in particular 0.5 min to 10 min, preferably 1 min to 5 min.

The applying of the nanofiber layer, in particular of the nanofibers, can be performed by means of electrospinning, a spun-bonding method, a melt-blow method, or a combination of the aforementioned methods, preferably by means of electrospinning or electrospinning methods.

It has proven advantageous according to the invention when the nanofiber layer, in particular the nanofibers, is/are applied to the support material at an area weight in the range from 0.2 g/m² to 60 g/m², in particular in the range from 0.5 g/m² to 40 g/m², preferably in the range from 0.8 g/m² to 20 g/m², preferably in the range from 0.9 g/m² to 10 g/m², particularly preferably in the range from 0.95 g/m² to 5 g/m², most particularly preferably in the range from 1 g/m² to 3 g/m².

In general, it can moreover be provided that the nanofiber layer, in particular the nanofibers, is/are applied to the support material at a thickness of the nanofiber layer or for obtaining a thickness of the nanofiber layer of at most 100 µm, in particular at most 50 µm, preferably at most 20 µm, preferably at most 10 µm, particularly preferably at most 5 µm.

In general, it can moreover by provided that the nanofiber layer, in particular the nanofibers, is/are applied to the support material at a thickness of the nanofiber layer or for obtaining a thickness of the nanofiber layer in the range from 0.001 µm to 100 µm, in particular in the range from 0.005 µm to 50 µm, preferably in the range from 0.008 µm to 20 µm, preferably in the range from 0.01 µm to 10 µm, particularly preferably in the range from 0.15 µm to 8 µm, most particularly preferably in the range from 1 µm to 7 µm, furthermore preferably in the range from 2 µm to 6 µm, even furthermore preferably in the range from 3 µm to 5 µm, yet even more preferably in the range from 4 µm to 5 µm.

It can furthermore be provided that the nanofiber layer, in particular the nanofibers, is/are applied to the support material at a density of the nanofiber layer or for obtaining a thickness of the nanofiber layer in the range from 10 kg/m³ to 1,000 kg/m³, in particular in the range from 100 kg/m³ to 800 kg/m³, preferably in the range from 150 kg/m³ to 500 kg/m³, preferably in the range from 200 kg/m³ to 300 kg/m³.

In the context of the method management according to the invention one can proceed in particular in such a manner that the nanofiber layer, in particular the nanofibers, is/are applied to, or brought to bond with, respectively, the support material in such a manner that a population of the support material by the nanofiber layer, in particular by the nanofibers, is performed across substantially the entire area. One should proceed herein such that at least 80%, in particular at least 90%, preferably at least 95%, preferably at least 99%, preferably at least 99.5%, of a (first) side of the support material is populated by the nanofiber layer, in particular by the nanofibers.

In general, the applying of the nanofiber layer 3, in particular of the nanofibers, should be performed to the at least substantially dried and/or cured, in particular cross-linked, support material.

According to the invention, the fixing, or bringing to bond, respectively, of the nanofiber layer, in particular of the nanofibers, on the support material herein can in particular be performed as a result of an inherent adhesiveness of the nanofibers which is in particular present in the production of the nanofibers.

Moreover, the applying of the nanofiber layer, in particular of the nanofibers, to the support material can be performed before or after, in particular after, applying the support material to the textile carrier.

In particular, the applying of the nanofiber layer, in particular of the nanofibers, to the support material can be performed before or after releasing the support material from the removable carrier layer.

According to the method management according to the invention, it can be moreover provided that the sheet filter material is furthermore (d) equipped or provided, respectively, with at least one covering layer. Consequently, an additional layer (d) in the form of a covering layer can be provided. In this context, the covering layer can be assigned to the nanofiber layer. In particular, the covering layer can be disposed on the (second) side of the nanofiber layer that faces away from the support material.

Moreover, according to the invention one can proceed in such a manner that the sheet filter material is furthermore (e) equipped or provided, respectively, with at least one adsorption layer. Accordingly, an additional layer (d) in the form of an adsorption layer can be provided. In this regard, the adsorption layer can be assigned to the support material. The adsorption layer can in particular be disposed on the (second) side of the support material that faces away from the nanofiber layer.

According to one preferred embodiment of the method according to the invention one can proceed in such a manner that the adsorption layer is not assigned to the nanofiber layer, or that the adsorption layer is not disposed between the support material and the nanofiber layer, respectively.

One can in particular also proceed in such a manner that the adsorption layer is not fixed to the support material, or not to the textile carrier, respectively. One can proceed in particular in such a manner that the adsorption layer is not brought to bond with the support material, or not with the textile carrier, respectively.

In the context of the present invention, an overall efficient method for producing the sheet filter material according to the invention is provided.

The present invention, according to a further aspect of the present invention, furthermore relates to the use of the sheet filter material defined above for the production of protective equipment and/or protective items of all manner, in particular of protective clothing, in particular for the civil or defense sector, such as protective suits, protective gloves, protective footwear, protective socks, protective headgear, or the like, and/or for the production of protective covers of all manner, preferably all aforementioned protective materials and/or items of protective clothing for use in ABC applications and/or having a protective function in relation to chemical, biological and/or radioactive harmful and toxic substances; or for the production of sports and/or leisurewear and/or sports and/or leisure equipment, such as sports and/or leisure pants and/or sports and/or leisure jackets, sports and/or leisure underwear, sports and/or leisure socks, sports and/or leisure gloves, sports and/or leisure headgear, and sports and/or leisure shoe materials, in particular sports and/or leisure footwear, preferably all aforementioned materials and/or items of clothing for outdoor use and/or having water-repellent (i.e. repelling water in liquid form) and/or wind-repellent and/or breathable (i.e. water-vapor-permeable and preferably also air-permeable) properties.

According to this aspect of the present invention, the present invention also relates to the use of the previously defined sheet filter material for the production of filters and filter materials of all manner, in particular for removing harmful, odorous, and toxic substances of all manner, preferably for removing chemical, biological and/or radioactive harmful and toxic substances, in particular from air flows and/or gas flows, such as ABC protection mask filters, odor filters, sheet filters, air filters, in particular filters for purifying room air, adsorption-capable support structures, and filters for the medical sector.

A subject matter of the present invention, according to a further aspect of the present invention, are moreover protective equipment and/or protective items of all manner, in particular for the civil or defense sector, in particular protective clothing such as protective suits, protective gloves, protective footwear, protective socks, protective headgear, and the like, as well as protective covers, preferably all aforementioned protective equipment and/or protective items for the use in ABC applications, and/or having a protective function in relation to chemical, biological and/or radioactive harmful and toxic substances; and/or sports and/or leisurewear and/or sports and/or leisure equipment of all manner, in particular for outdoor use, and/or having water-repellent (ie. repelling water in liquid form) and/or wind-repellent and/or breathable (ie. water-vapor-permeable and preferably also air-permeable) properties, such as sports and/or leisure pants and/or sports and/or leisure jackets, sports and/or leisure underwear, sports and/or leisure socks, sports and/or leisure gloves, sports and/or leisure headgear, and sports and/or leisure shoe materials, in particular sports and/or leisure footwear, in each case produced while using the previously described sheet filter material 1 according to the invention and/or comprising the previously described sheet filter material 1 according to the invention.

Finally, a further subject matter of the present invention, according to a further aspect of the present invention, are also filters and filter materials of all manner, in particular for removing harmful, odorous, and toxic substances of all manner, preferably for removing chemical, biological and/or radioactive harmful and toxic substances in particular from air flows and/or gas flows, such as protection mask filters, odor filters, sheet filters, air filters, in particular filters for cleaning room air, adsorption-capable support structures, and filters for the medical sector, produced while using the previously described sheet filter material 1 according to the invention and/or comprising the previously described sheet filter material 1 according to the invention.

Further design embodiments, variants, variations, modifications, particularities and advantages of the present invention are readily obvious to the person skilled in the art when reading the description, and can be implemented without said person skilled in the art departing from the scope of the present invention.

The present invention will be visualized by means of the following exemplary embodiments which are however not in any way intended to limit the present invention.

Exemplary Embodiments

1. Dissimilar sheet filter materials will be produced, specifically
   A) a sheet filter material A according to the invention, which has a foam-based or foam-shaped, respectively support material which is applied to a textile carrier and has a nanofiber layer attached thereto, wherein the nanofiber layer is disposed on the side of the support material which faces away from the textile carrier, and wherein the foam-based or foam-shaped, respectively, support material and the nanofiber layer have identical layer thicknesses;
   B) a sheet filter material B (comparison) which has a foam-based or foam-shaped, respectively, support material which is applied to a textile carrier, but does not have any nanofiber layer, wherein the thickness of the support material corresponds to the overall thickness of the composite of the foam-based or foam-shaped, respectively, support material and nanofiber layer present in the material A; material B thus has a foam-based or foam-shaped, respectively, support material having a thickness which is double in comparison to material A and moreover does not have any nanofiber layer;
   C) a sheet filter material C (comparison) which has a nanofiber layer which is applied to a textile carrier, but does not have any foam-based or foam-shaped, respectively, support material, wherein the thickness of the nanofiber layer corresponds to the overall thickness of the composite of foam-based or foam-shaped, respectively, support material and nanofiber layer present in the material A; material C thus has a nanofiber layer having a thickness which is double in comparison to material A, and moreover does not have any foam-based or foam-shaped, respectively, support material.
   A', B', C') Moreover, further sheet filter materials A' (according to the invention) as well as B' (comparison) and C' (comparison) are provided, each corresponding to the respectively corresponding sheet filter materials A, B, and C, with the provision that the sheet filter materials A', B', and C' are equipped or upgraded, respectively, with an adsorption material in the form of particulate activated carbon, said absorption material being fixed on a further textile carrier, wherein the composite of activated carbon and further textile carrier is loosely disposed on the side of the first textile carrier that faces away from the foam-based or foam-shaped, respectively, support material in such a manner that the activated carbon is positioned between the first textile carrier and the further textile carrier.

In order for the aforementioned sheet filter material A to be produced, a textile carrier layer having an area weight of approximately 75 g/m$^2$ is used as the textile carrier. In order for the foam-based or foam-shaped, respectively, support material to be provided, the textile carrier is coated across the entire face with an aqueous solution or dispersion, respectively, of a foam structure material (foam structure polymer) based on a polyurethane (PU), said solution or dispersion, respectively, having previously been foamed by the introduction of mechanical energy, wherein the adhesive layer in the form of the foamed solution or dispersion, respectively, is squeegeed onto the carrier. The applied foam-based material in the form of the solution or dispersion, respectively, has a density of approximately 210 g/l at a solids content of approximately 55% in terms of the solution or dispersion, respectively. The solution or dispersion, respectively, is applied at a defined quantity so as to subsequently obtain a predefined thickness. Drying or curing, respectively, of the solution or dispersion, respectively, of the foam structure material takes place while introducing energy in order for a dried or cured, respectively, broken or open-pored, respectively, support material or foam, respectively, to be configured. The drying or curing, respectively, herein takes place at temperatures between 100° C. and 140° C. The resultant layer in the form of the support material has a defined thickness in the range of magnitude stated according to the invention. A nanofiber layer based on a polyurethane is subsequently applied to the thus obtained foam-based or foam-shaped, respectively, support material by means of electrospinning, wherein the underlying nanofibers by virtue of the inherent adhesiveness present in the production of said nanofibers are fixed to the support material. The nanofibers herein have fiber diameters in the range from 100 nm to 500 nm. The nanofiber layer is applied at a predefined layer thickness, the latter corresponding to that of the foam-based or foam-shaped, respectively, support material. A triple-layered material in the form of a foam-based or foam-shaped, respectively, support material on a textile carrier having a nanofiber layer applied thereto thus results.

The production of the sheet filter material B takes place as has been described in the context of the sheet filter material A, however with the provision that the foam-based or foam-shaped, respectively, support material is fixed to the textile carrier at double thickness, and that moreover no nanofiber layer is applied. A double-layered material in the form of a foam-based or foam-shaped, respectively, support material which is applied to a textile carrier at double thickness thus results.

Furthermore, the production of the sheet filter material C takes place as has been described in the context of the sheet filter material A, however with the provision that the nanofiber layer is fixed immediately and at double thickness on the textile carrier. A double-layered material in the form of a nanofiber layer applied to a textile carrier with double thickness thus results.

For the production of the further sheet filter materials A', B' and C' one moreover proceeds in such a manner that a particulate activated carbon (particle diameter approximately 0.3 mm) at an application quantity of approximately 70 g/m² is fixed on a further textile carrier (area weight approximately 75 g/m²) while using a bonding agent (adhesive based on polyurethane) which is applied in a discontinuous/punctiform manner, wherein an almost complete population of a flat side of the further textile carrier with the activated carbon results. The thus obtained further carrier equipped with the activated carbon is combined with the corresponding materials A, B, and C, respectively, and specifically such that the further textile carrier equipped with the activated carbon is in each case disposed on the side of the first textile carrier that faces away from the foam-based or foam-shaped, respectively, support material (materials A and B) or faces away from the nanofiber layer (material C), respectively, or is brought to loosely connect with the first carrier, wherein the activated carbon is positioned between the first carrier and the second carrier (wherein the activated carbon is fixedly connected to the further textile carrier and bears loosely on the first textile carrier, or is in loose contact with the latter, respectively).

2. The aforementioned sheet filter materials A, B and C are tested as follows:
    a) First, the separation factor performance according to DIN EN 1822 (April 1998) and the mean separation factor $A_m$ according to DIN EN 779 (July 1993) are in each case determined on the sheet filter materials A, B and C. The separation factor performance according to DIN EN 1822 (April 1998) for the sheet filter material A is approximately 96%, and the mean separation factor $A_m$ according to DIN EN 779 (July 1993) is approximately 99%. For the sheet filter material B, respective values are approximately 80% for the separation factor performance, and approximately 85% for $A_m$, while values of approximately 92% for the separation factor performance and of approximately 96% for $A_m$ have been determined for the sheet filter material C.
    Furthermore, the integral initial transmittance $D_i$ according to DIN EN 1822 (April 1998; DEHS-Aerosol, MPPS=0.1 to 0.3 µm) is determined. The integral initial transmittance $D_i$ herein is approximately 2% for the sheet filter material A, while a value of approximately 8% results for the sheet filter material B, and a value of approximately 4% results for the sheet filter material C.
    Moreover, the sheet filter material A in relation to particles and aerosols having diameters ≥1 µm has a separation factor above 98.5%, while a value of approximately 90% results for the sheet filter material B, and a value of approximately 95% results for the sheet filter material C.
    The explanations above demonstrate that the sheet filter material A according to the invention overall has improved aerosol or particle filter properties, respectively.
    b) Moreover, a washing test (DIN EN ISO 5077) is carried out on the sheet filter materials A, B, and C. The sheet filter material A according to the invention has better values in comparison to the sheet filter materials B and C. Sheet filter material B has only an adequate wash resistance, and satisfactory values in terms of the wash resistance can at best be determined for the sheet filter material C.
3. The aforementioned sheet filter materials A', B' and C' are tested in terms of the protective function thereof in relation to harmful and toxic substances.
    The barrier effect in relation to mustard gas is determined herein according to method 2.2 of CRDEC-SP-84010 in the context of the so-called convective flow test. For this purpose, an airflow containing mustard gas is allowed to act on the respective sheet filter material at a constant flow resistance at a constant flow rate of approximately 0.45 cm/s, and the area-related breakthrough quantity is determined after 16 hours (80% relative humidity, 32° C.). The breakthrough quantity for the sheet filter material A' according to the invention is 2.2 µg/cm², while a value of 3 µg/cm² can be determined for the sheet filter material B', and a value of 2.7 µg/cm² can be determined for the sheet filter material C'.
4. Moreover, following the above explanations, further sheet filter materials are produced, specifically having a variable layer thickness of the foam-based or foam-shaped support material (0.3 µm to 0.1 µm) and having a constant layer thickness of the nanofiber layer (4 µm), specifically
    A1) a sheet filter material A1 according to the invention, which has a foam-based or foam-shaped support material which is applied to a textile carrier and has a nanofiber layer fixed thereto, wherein the nanofiber layer is disposed on the side of the support material that faces away from the textile carrier, and wherein the foam-based or foam-shaped, respectively, support material has a layer thickness of 0.3 µm, while the layer thickness of the nanofiber layer is 4 µm;
    A2) a sheet filter material A2 according to the invention, which corresponds to the sheet filter material A1 with the provision that the foam-based or foam-shaped support material has a layer thickness of 0.2 µm; as well as
    A3) a sheet filter material A2 according to the invention, which corresponds to the sheet filter material A1 with the provision that the foam-based or foam-shaped, respectively, support material has a layer thickness of 0.1 µm.

The tests set forth in section 2.) are carried out on the afore-mentioned sheet filter materials (determination of the separation factor performance according to DIN EN 1822 (April 1998), of the mean separation factor $A_m$ according to DIN EN 779 (July 1993) and of the integral initial transmittance $D_i$ according to DIN EN 1822 (April 1998; DEHS-Aerosol, MPPS=0.1 to 0.3 µm); moreover, a washing test (DIN EN ISO 5077) is carried out). The sheet filter materials A1 to A3 according to the invention herein have properties which are fundamentally comparable to those of the sheet filter material A according to the invention. It is moreover demonstrated that the properties in question are improved as the thickness increases (A1>A2>A3).

The above tests overall show the outstanding properties of the sheet filter materials according to the invention.

LIST OF REFERENCE SIGNS

1 Sheet filter material
2 Foam-based and/or foam-shaped support material
2a (First) side of the foam-based and/or foam-shaped support material
2b (Second) side of the foam-based and/or foam-shaped support material
3 Nanofiber layer
3a (First) side of the nanofiber layer
3b (Second) side of the nanofiber layer
3' Nanofibers
4 Textile carrier
4a (First) side of the textile carrier
4b (Second) side of the textile carrier
5 Covering layer
5a (First) side of the covering layer
5b (Second) side of the covering layer
6 Adsorption layer
6a (First) side of the adsorption layer
6b (Second) side of the adsorption layer

The invention claimed is:

1. A sheet filter material having an aerosol and particle filter function and further providing a protective function in relation to chemical, biological and radioactive harmful and toxic substances, wherein the sheet filter material comprises: (a) an air-permeable and water-vapor-permeable, planar foam-based support material having two opposite flat sides, wherein the support material is an air-permeable and discontinuously configured layer based on a dried and cured, cross-linked broken polymer foam structure, wherein the broken polymer foam structure is configured so as to be open-pored; (b) an air-permeable and water-vapor-permeable, planar nanofiber layer which is fixed to a first flat side of the foam-based support material, wherein the nanofiber layer comprises a multiplicity of nanofibers; and (c) at least one adsorption layer, wherein the adsorption layer comprises a multiplicity of individual and discrete adsorber particles and wherein the adsorption layer has two opposite flat sides, wherein the adsorption layer is disposed on the second flat side of the support material that faces away from the nanofiber layer.

2. The sheet filter material as claimed in claim 1, wherein the support material has an area weight in the range from 5 g/m² to 500 g/m²,
wherein the support material has a thickness in the range from 0.01 mm to 10 mm, and
wherein the support material has a density in the range of from 25 g/l to 250 g/l.

3. The sheet filter material as claimed in claim 1,
wherein the broken polymer foam structure comprises a multiplicity of dried or cured, cross-linked, destroyed or burst or collapsed foam bubbles.

4. The sheet filter material as claimed in claim 1,
wherein the broken polymer foam structure comprises a multiplicity of destroyed, broken or collapsed walls or webs formed from a polymer foam structure material; and
wherein the broken polymer foam structure comprises a proportion of destroyed, burst or collapsed foam bubbles in the range of from 10% up to 95%, in terms of the overall number of foam bubbles in the broken polymer foam structure.

5. The sheet filter material as claimed in claim 1,
wherein the broken polymer foam structure comprises a multiplicity of breakthroughs, pores, ducts or openings extending within the broken polymer foam structure and connecting the two flat sides of the support material.

6. The sheet filter material as claimed in claim 1,
wherein the broken polymer foam structure is configured so as to be contiguous and coherent.

7. The sheet filter material as claimed in claim 1,
wherein the nanofiber layer has two opposite flat sides.

8. The sheet filter material as claimed in claim 1,
wherein the nanofiber layer is fixed to the first flat side of the support material at least substantially across the entire area of a first flat side of the nanofiber layer.

9. The sheet filter material as claimed in claim 1,
wherein the nanofiber layer is fixed to the first flat side of the support material without the use of a bonding agent.

10. The sheet filter material as claimed in claim 1,
wherein the nanofiber layer is configured as a planar or three-dimensional textile formation comprising the nanofibers.

11. The sheet filter material as claimed in claim 1,
wherein the nanofibers are disposed randomly and in a non-oriented manner in the nanofiber layer; and
wherein the nanofibers are bonded to one another, within the nanofiber layer, by means of an inherent adhesiveness of the nanofibers.

12. The sheet filter material as claimed in claim 1,
wherein the nanofiber layer is configured as a cross-laid fabric or a textile composite cloth; and
wherein the nanofiber layer has a thickness in the range of from 0.001 μm to 100 μm.

13. The sheet filter material as claimed in claim 1,
wherein the nanofibers have mean fiber diameter $D_{50}$ in the range of from 2 nm to 4,500 nm; and
wherein the nanofiber layer has openings or pores which are delimited by the nanofibers, wherein the nanofiber layer has a mean openings or pore size of at most 150 μm.

14. The sheet filter material as claimed in claim 1,
wherein the nanofibers have a mean fiber diameter $D_{50}$ in the range of from 2 nm to 4,500 nm; and
wherein the nanofiber layer has openings or pores which are delimited by the nanofibers, wherein the ratio of the mean opening or pore size to the mean fiber diameter $D_{50}$ of the nanofibers, on the other hand, is in the range from 0.2 to 1,800.

15. The sheet filter material as claimed in claim 1,
wherein the sheet filter material furthermore comprises at least one textile carrier.

16. The sheet filter material as claimed in claim 15,
wherein the textile carrier is fixed to the support material and
wherein the textile carrier is configured as an air-permeable and water-vapor-permeable textile material.

17. The sheet filter material as claimed in claim 1,
wherein the sheet filter material furthermore comprises at least one covering layer.

18. The sheet filter material as claimed in claim 17,
wherein the covering layer is configured as an air-permeable and water-vapor-permeable textile material.

19. The sheet filter material as claimed in claim 1,
wherein the sheet filter material is configured as a self-supporting composite material,
wherein the sheet filter material has an overall area weight in the range of from 10 g/m² to 800 g/m²;
wherein the sheet filter material has an air permeability of at least 10 l·m⁻²·s⁻¹ at a flow resistance of 127 Pa;
wherein the sheet filter material at 25° C. has a water-vapor permeability of at least 10 l/m² per 24 h; and
wherein the sheet filter material has a water-vapor transmittance resistance $R_{et}$ at stationary conditions, measured according to DIN EN 31 092:1993 (February 1994) and international standard ISO 11 092, at 35° C., of at most 25 (m²·Pascal)/Watt.

20. The sheet filter material as claimed in claim 1,
wherein the sheet filter material has an overall thickness in the range of from 0.1 mm to 30 mm.

21. A method for producing a sheet filter material as defined in claim 1,
wherein the method comprises the following steps:
providing an air-permeable and water-vapor-permeable planar foam-based support material having two opposite flat sides, wherein the support material is an air-permeable and discontinuously configured layer based on a dried and cured, cross-linked broken polymer foam structure, wherein the broken polymer foam structure is configured so as to be open-pored and/or not to be closed;
applying an air-permeable and water-vapor-permeable, planar nanofiber layer comprising a multiplicity of nanofibers on a first flat side of the foam-based support material in such a manner that the nanofiber layer is fixed to the first flat side of the support material;
wherein the sheet filter material is furthermore provided with at least one adsorption layer comprising a multiplicity of individual and discrete adsorber particles, wherein the adsorption layer has two opposite flat sides, wherein the adsorption layer is disposed on the second side of the support material that faces away from the nanofiber layer.

22. A protective equipment comprising a sheet filter material as defined in claim 1.

23. The protective equipment as claimed in claim 22,
wherein the protective equipment is selected from the group consisting of protective items for the civil or defense sector, protective clothing, protective suits, protective gloves, protective footwear, protective socks, protective headgear, protective covers, protective items for the use in NBC applications, protective equipment having a protective function in relation to chemical, biological, and radioactive harmful and toxic substances as well as protective items having a protective function in relation to chemical, biological, and radioactive harmful and toxic substances.

24. The protective equipment as claimed in claim 22,
wherein the protective equipment is selected from the group consisting of sports and leisure wear, sports and leisure equipment, sports and leisure equipment for outdoor use, sports and leisure equipment having water-repellent, wind-repellent and breathable properties, sports and leisure pants, sports and leisure jackets, sports and leisure underwear, sports and leisure socks, sports and leisure gloves, sports and leisure headgear, sports and leisure shoe materials and sports and leisure footwear.

25. A filter comprising a sheet filter material as defined in claim 1.

26. The filter as claimed in claim 25,
wherein the filter is selected from the group consisting of filters and filter materials for removing harmful, odorous or toxic substances, filters and filter materials for removing chemical, biological or radioactive harmful and toxic substances, filters and filter materials for removing chemical, biological or radioactive harmful and toxic substances from air flows or gas flows, protection mask filters, odor filters, sheet filters, air filters, filters for cleaning room air, adsorption-capable support structures, and filters for the medical sector.

\* \* \* \* \*